United States Patent [19]

Hiratsuka et al.

[11] Patent Number: 5,424,275
[45] Date of Patent: Jun. 13, 1995

[54] BIPHENYL DERIVATIVES AND THEIR USE AS HERBICIDES

[75] Inventors: Mitsunori Hiratsuka, Oita; Toru Uekawa, Takarazuka; Naonori Hirata, Sanda; Kazuo Saito, Toyonaka; Hiroyuki Yogai, Ibaraki, all of Japan

[73] Assignee: Sumitomo Chemical Company, Limited, Osaka, Japan

[21] Appl. No.: 135,961

[22] Filed: Oct. 14, 1993

[30] Foreign Application Priority Data

Oct. 16, 1992 [JP] Japan ................................. 4-278475
Oct. 19, 1992 [JP] Japan ................................. 4-279924

[51] Int. Cl.⁶ ............... C07D 239/32; C07D 239/46; C07D 239/60; A01N 43/54
[52] U.S. Cl. ............... 504/243; 504/242; 504/221; 504/235; 504/225; 544/301; 544/302; 544/312; 544/313; 544/314; 544/319; 544/316; 544/318; 544/295; 544/122; 544/123; 544/58.2; 544/58.6
[58] Field of Search ............... 504/242, 243, 221, 235, 504/225; 544/301, 302, 312, 313, 314, 319, 316, 318, 295, 122, 123, 58.2, 58.6

[56] References Cited

FOREIGN PATENT DOCUMENTS

| | | |
|---|---|---|
| 0346789 | 12/1989 | European Pat. Off. |
| 0402751 | 12/1990 | European Pat. Off. |
| 0426476 | 5/1991 | European Pat. Off. |
| 0468690 | 1/1992 | European Pat. Off. |
| 0469711 | 2/1992 | European Pat. Off. |
| 0549344 | 6/1993 | European Pat. Off. |
| 4126936 | 8/1991 | Germany. |
| 4112876 | 8/1990 | Japan. |
| 91/13065 | 9/1991 | WIPO. |

*Primary Examiner*—John M. Ford
*Attorney, Agent, or Firm*—Stevens, Davis, Miller & Mosher

[57] ABSTRACT

Novel biphenyl derivatives represented by the formula (I)

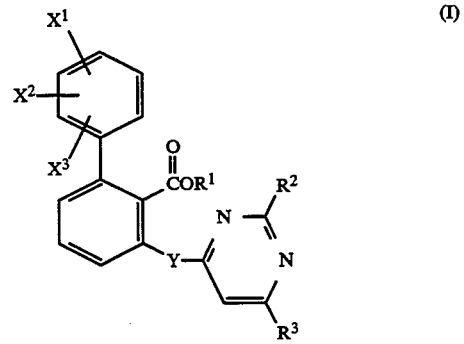

wherein $R^1$, $R^2$, $R^3$, $X^1$, $X^2$, $X^3$ and Y are as defined hereinafter.

12 Claims, No Drawings

BIPHENYL DERIVATIVES AND THEIR USE AS HERBICIDES

The present invention relates to a novel biphenyl derivative, a method for producing the same and its use as herbicides.

It is described in EP 402751 and EP 346789 that certain kinds of compounds can be used as active ingredients for herbicides.

However, these compounds are not always said to be satisfactory because they are insufficient as herbicides.

In view of these circumstances, the present inventors have extensively studied, and as a result, have found that a biphenyl derivative represented by the following formula (I) is an excellent compound as herbicides which can control weeds widely generated in crop lands or non-crop lands at low dosage raze, has a broad herbicidal spectrum and also can safely be used for no-till cultivation. The present invention is based on this finding.

The present invention provides a biphenyl derivative represented by the formula (I) [hereinafter referred to as the present compound(s)], a method for producing the same and its use as herbicides:

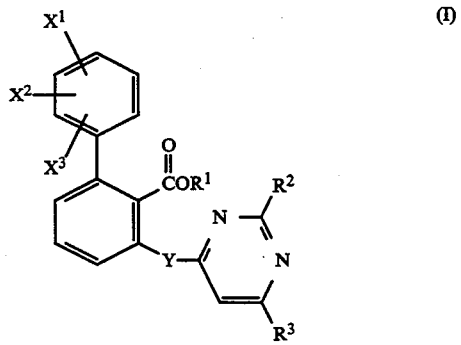

wherein $R^1$ represents a hydrogen atom or a group represented by the formula

(wherein each of $R^4$ and $R^5$ which may be the same or different, represents a hydrogen atom, a $C_1$–$C_6$ alkyl group, a $C_3$–$C_8$ cycloalkyl group, or a phenyl group optionally substituted with at least one member selected from the group consisting of $C_1$–$C_6$ alkyl groups, halogen atoms and $C_1$–$C_6$ alkoxy groups, or a benzyl group optionally substituted with at least one member selected from the group consisting of $C_1$–$C_6$ alkyl groups, halogen atoms and $C_1$–$C_6$ alkoxy groups, or $R^4$ and $R^5$ are bonded together at their ends to form a $C_4$–$C_6$ alkylene group optionally substituted with $C_1$–$C_6$ alkyl groups; or $R^4$ and $R^5$ are bonded together at their ends to form a $C_4$–$C_6$ alkylene group containing one or more hereto atoms selected from the group consisting of oxygen, sulfur and nitrogen atoms, optionally substituted with $C_1$–$C_6$ alkyl groups), each of $R^2$ and $R^3$, which may be the same or different, represents a $C_1$–$C_6$ alkyl group, a halo $C_1$–$C_6$ alkoxy group, a $C_1$–$C_6$ alkylthio group, a halo $C_1$–$C_6$ alkoxy group or a halogen atom, each of $X^1$, $X^2$ and $X^3$, which may be the same or different, represents a hydrogen atom, a hydroxyl group, a $C_1$–$C_6$ alkyl group, a halo $C_1$–$C_6$ alkyl group, a $C_1$–$C_6$ alkoxy group, a nitro group, a cyano group or a halogen atom and Y represents an oxygen atom or a sulfur atom; or agriculturally acceptable salts thereof.

In the compound of the formula (I), each of $R^2$ and $R^3$, which may be the same or different, is preferably a $C_1$–$C_6$ alkoxy group, and more preferably both of them are methoxy groups; Y is preferably an oxygen atom; each of $R^4$ and $R^5$, which may be the same or different, is preferably a $C_1$–$C_3$ alkyl group, and more preferably both of $R^4$ and $R^5$ are methyl groups;

examples of the $C_1$–$C_6$ alkyl groups and alkyl moiety of the $C_1$–$C_6$ alkylthio group include methyl, ethyl, n-propyl, i-propyl, n-butyl, sec-butyl, tert-butyl, n-hexyl groups and the like;

examples of the $C_1$–$C_6$ alkoxy groups and alkoxy moiety of the halo $C_1$–$C_6$ alkoxy groups include methoxy, ethoxy, n-propoxy, i-propoxy, n-butoxy, n-hexyloxy groups and the like;

examples of the $C_3$–$C_8$ cycloalkyl groups include cyclopropyl, cyclobutyl, cyclopentyl, cyclohexyl, cycloheptyl, cyclooctyl groups and the like;

examples of the halogen atom and halogen moiety of the halo $C_1$–$C_6$ alkoxy groups include fluorine, chlorine and bromine;

examples of the halo $C_1$–$C_6$ alkyl groups include trifluoromethyl, 2-chloroethyl, 2-bromoethyl, 3-fluoropropyl, 2-chloropropyl, 4-chlorobutyl, 6-chlorohexyl groups and the like;

examples of the $C_1$–$C_6$ haloalkoxy groups include fluoromethoxy, dibromomethoxy, trifluoromethoxy, 1,1,2,2-tetrafluorohexyloxy, 1,1-dichloroethoxy, 1-chloro-2-bromobutoxy groups and the like;

examples of the $C_4$–$C_6$ alkylene group optionally substituted with $C_1$–$C_6$ alkyl groups include tetramethylene, pentamethylene, hexamethylene, 1,4-dimethyltetramethylene, 1,5-dimethylpentamethylene, 1-methylpentamethylene, 2-methylpentamethylene, 2-ethypentamethylene, 2-butylpentamethylene, 2-hexyltetramethylene;

examples of the $C_4$–$C_6$ alkylene group having one or more hetero atoms selected from the group consisting of oxygen, sulfur and nitrogen atoms, optionally substituted with $C_1$–$C_6$ alkyl groups include:

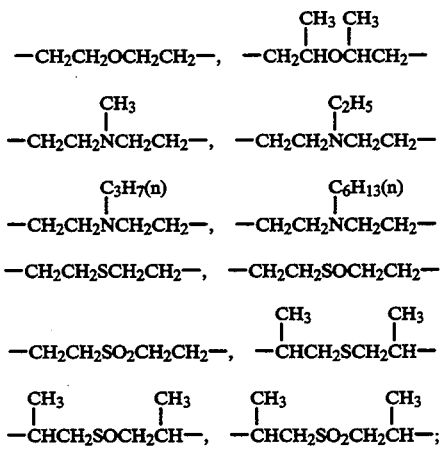

examples of the phenyl group or benzyl group, optionally substituted with at least one member selected from the group consisting of $C_1$–$C_6$ alkyl groups, halogen atoms, and $C_1$–$C_6$ alkoxy groups include 3-methoxyphenyl, 3-ethoxyphenyl, 4-i-propoxyphenyl, 3-hexyloxyphenyl, 2-fluorophenyl, 3-fluorophenyl, 2-chlorophenyl, 3-bromophenyl, 2,4-dichlorophenyl, 2,6-difluorophenyl, 2-methylphenyl, 3-ethylphenyl, 4-hexylphenyl, 2,6-dimethylphenyl, 2,4,6-trimethylphenyl, 2-chloro-4-methylphenyl, 2-fluoro-4-methoxyphenyl groups, 3-methoxybenzyl, 3-ethoxybenzyl, 4-i-propoxybenzyl, 3-hexyloxybenzyl, 2-fluorobenzyl, 3-fluorobenzyl, 2-chlorobenzyl, 3-bromobenzyl, 2,4-dichlorobenzyl, 2-methylbenzyl, 3-ethylbenzyl, 4-hexylbenzyl, 2,6-dimethylbenzyl, 2-chloro-4-methylbenzyl, 2-fluoro-4-methoxybenzyl groups and the like.

The agriculturally acceptable salts of the compound (I) is

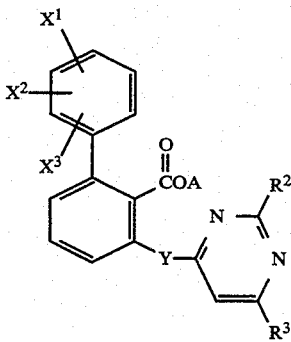

wherein A includes the cation of alkaline metals such as sodium, potassium, lithium, etc., the cation of alkaline earth metals such as magnesium, calcium, etc., ammonium group which may be substituted with alkyl groups, etc., such as isopropylammonium, hexylammonium, etc., and the like.

A method for producing the present compound is as follows:

The present compound (I) wherein $R^1$ is a hydrogen atom, which is referred as compound (I)' hereinafter, can be produced by reacting (reaction (a)) a compound represented by the formula (II)

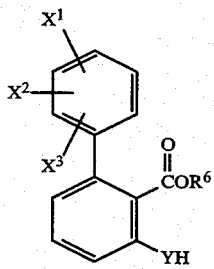

wherein $X^1$, $X^2$, $X^3$ and Y are as defined above and $R^6$ represents a $C_1$–$C_6$ alkyl group or a benzyl group, with a compound (III)

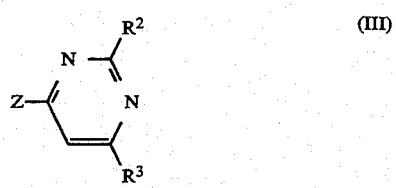

wherein $R^2$ and $R^3$ are each as defined above and Z represents a halogen atom or an alkylsulfonyl group, to produce a compound (IV)

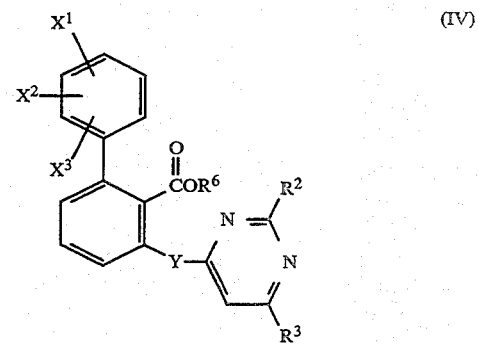

(wherein $R^2$, $R^3$, $R^6$, $X^1$, $X^2$, $X^3$ and Y are as defined above), and subsequently hydrolyzing (reaction (b)) the compound (IV) in the presence of a base or an acid.

When $R^6$ is a benzyl group, the compound (IV) can also be subjected to catalytic reduction to obtain the compound (I)'.

This reaction (a) is usually carried out with or without a solvent in the presence of a base. The reaction temperature usually ranges from room temperature to the boiling point of the solvent, and the reaction time ranges from 10 minutes to 24 hours. Referring to the amounts of the reagents used for this reaction, the amount of the compound (III) is 1 to 3 equivalents based on 1 equivalent of the compound (II), and that of the base is 1 to 5 equivalents based on the same. The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), liquid ammonia, water and mixtures thereof.

The base includes organic bases (e.g. pyridine, triethylamine, N,N-diethylaniline), inorganic bases (e.g. sodium hydroxide, potassium hydroxide, sodium carbonate, potassium carbonate, sodium hydride), alkaline metal alkoxide (e.g. sodium methoxide, sodium ethoxide), etc.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound (IV) can be obtained.

The reaction (b) (hydrolysis) is usually carried out with or without a solvent in the presence of an acid or a base.

Generally, the reaction temperature ranges from room temperature to the boiling point of the solvent. The reaction time ranges from 10 minutes to 48 hours.

The amount of acid or base used is 0.01 to 100 equivalents based on 1 equivalent of the compound represented by the formula (IV).

Such a base includes sodium hydroxide, potassium hydroxide, sodium carbonate, potassium carbonate, etc. Such an acid includes HCl, $H_2SO_4$, etc. The solvent includes aliphatic hydrocarbons (e.g. hexane, heptane, ligroin, petroleum ether), aromatic hydrocarbons (e.g. benzene, toluene, xylene), halogenated hydrocarbons (e.g. chlorobenzene, dichlorobenzene), alcohols (e.g. methanol, ethanol, isopropanol, tert-butanol, octanol, cyclohexanol, diethylene glycol, glycerine), ethers (e.g. diethyl ether, diisopropyl ether, dioxane, tetrahydrofuran, diethylene glycol dimethyl ether), tertiary amines (e.g. pyridine, triethylamine, N,N-diethylaniline, tributylamine, N-methylmorpholine), water and mixtures thereof.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired compound (I)' can be obtained.

The catalytic reduction is usually carried out with or without a solvent in the presence of a catalyst. The reaction temperature usually ranges from room temperature to 200° C., and the reaction time ranges from 10 minutes to 48 hours. The reaction can be carried out under pressure. The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitriles (e.g. acetonitrile, isobutyronitrile), alcohols (e.g. methanol, ethanol, isopropanol, tert-butanol, octanol, cyclohexanol, 2-ethoxyethanol, diethylene glycol, glycerine), tertiary amines (e.g. pyridine, triethylamine, N,N-diethylaniline, tributylamine, N-methylmorpholine), aliphatic acids (e.g. formic acid, acetic acid), water and mixtures thereof. The catalyst includes palladium on carbon, platinum oxide, Raney nickel, etc. After completion of the reaction, the reaction solution is filtered to remove the catalyst, and then is after-treated as usual.

The agriculturally acceptable salts of the compound (I)' can be produced by reacting the compound (I)' with a base.

This reaction is usually carried out with or without solvent. Generally, the reaction temperature ranges from room temperature to the boiling point of the solvent and the reaction time ranges from 10 minutes to 24 hours. The amount of base used is 1 equivalent or more based on 1 equivalent of the compound (I)'.

The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. methyl ethyl ketone, methyl isobutyl ketone, isophorone), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), liquid ammonia, water and mixtures thereof.

Such a base include, carbonate, hydride and hydroxide, etc. of alkaline metal, alkaline earth metal etc., (e.g. lithium hydroxide, sodium hydroxide, potassium hydroxide, sodium carbonate, potassium carbonate, lithium hydride, sodium hydride, potassium hydride, calcium hydride, lithium methoxide, sodium methoxide, sodium ethoxide), alkaline metal (e.g. lithium, sodium, potassium), alkaline earth metal (e.g. magnesium, calcium), amines optionally substituted with alkyl groups (e.g. methylamine, ethylamine, propylamine, isopropylamine, butylamine, pentylamine, hexylamine), ammonia, etc.

After completion of the reaction, the reaction solution is after-treated as usual.

The present compound (I) (wherein $R^1$ is

($R^4$ and $R^5$ are as defined above)) can be produced by reacting the compound represented by the formula (V)

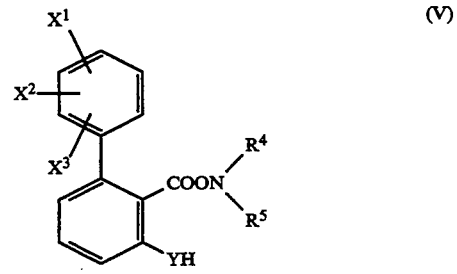

(V)

[wherein $X^1$, $X^2$, $X^3$, $R^4$, $R^5$ and Y are as defined above], with the compound represented by the formula (III).

This reaction is usually carried out according to the foregoing reaction (a).

The present compound (I) (wherein $R^1$ represents

wherein $R^4$ and $R^5$ are as defined above) can also be produced by reacting [reaction (i)] the present compound (I)' with an acid-halogenating agent or an active esterifying agent, and subsequently reacting [reaction (ii)] the resulting reaction product with the compound represented by the formula (VI),

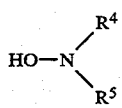

(wherein $R^4$ and $R^5$ are as define above).

In the above reaction (i), the acid-halogenating agent includes thionyl chloride, thionyl bromide, phosphorus trichloride, phosphorus tribromide, phosphorus pentachloride, phosphorus oxychloride, phosgene, oxalyl chloride, etc. The active esterifying agent includes N,N'-disubstituted carbodiimides such as N,N'-dicyclohexylcarbodiimide, N,N'-diisopropylcarbodiimide, 1-ethyl-3-(3-dimethylaminopropyl)carbodiimide hydrochloride, etc.; arylsulfonyl chlorides such as 2,4,6-trimethylbenzenesulfonyl chloride, 2,4,6-triisopropylbenzenesulfonyl chloride, etc.; N,N'-carbonyldiimidazole; diphenylphosphorylazide; N-ethoxycarbonyl-2-ethoxy-1,2-dihydroquinoline; N-ethyl-2'-hydroxybenzisoxazolim tetrafluoroborate; N-ethyl-5-phenylisoxazolium-3'-sulfonate; etc.

By this reaction, a pyrimidine derivative represented by the formula (VII),

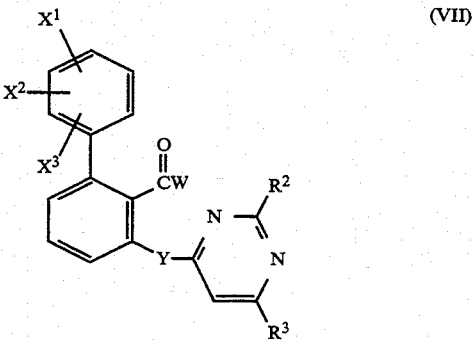

wherein $X^1$, $X^2$, $X^3$, $R^2$, $R^3$ and Y are as defined above, is produced in the reaction system.

In the above formula (VII), the substituent W represents a halogen atom when the acid-halogenating agent was used; W represents an N,N'-disubstituted-2-isoureide group when N,N'-disubstituted carbodiimide was used as the active esterifying agent; W represents an arylsulfonyloxy group when arylsulfonyl chloride was used as said agent; W represents an imidazolyl group when N,N'-carbonyldiimidazole was used as said agent; W represents an azide group when diphenylphosphorylazide was used as said agent; W represents an ethoxycarbonyloxy group when N-ethoxycarbonyl-2-ethoxy-1,2-dihydroquinoline was used as said agent; W represents 3-(N-ethylaminocarbonyl)-2-hydroxyphenoxy group when N-ethyl-2'-hydroxybenzisoxazolium tetrafluoroborate was used as said agent; and W represents a group

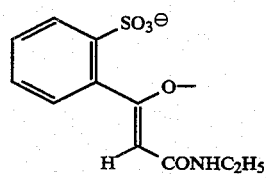

when N-ethyl-5-phenylisoxazolium-3'-sulfonate was used as said agent.

In the reaction system, W can also take a form of an acid anhydride represented by the formula,

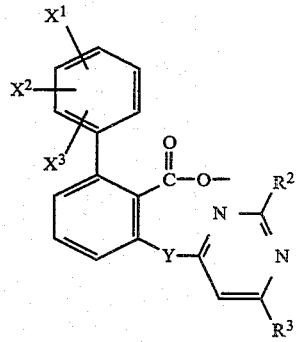

(wherein $X^1$, $X^2$, $X^3$, $R^2$, $R^3$ and Y are as defined above).

The amount of the foregoing acid-halogenating agent or active esterifying agent used is usually 1 to 10 equivalents based on 1 equivalent of the present compound (I)'.

The amount of the compound of the formula (VI) used is usually 1 to 5 equivalents based on 1 equivalent of the present compound (I)'.

The reactions (i) and (ii) can also be carried out, if necessary, in the presence of a base. Such a base includes organic bases (e.g. 1-methylimidazole, 3-nitro-1H-1,2,4-triazole, 1H-tetrazole, 1H-1,2,4-triazole, imidazole, pyridine, triethylamine) and inorganic bases (e.g. potassium carbonate). The amount of the base used is 1 to 20 equivalents based on 1 equivalent of the present compound (I)'.

The reactions (i) and (ii) are usually carried out in the presence of an inert solvent. Such a solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. N,N-dimethylformamide), sulfur compounds (e.g. dimethyl sulfoxide, sulfolane) and mixtures thereof.

Generally, the reaction temperature ranges from 0° C. to the boiling point of the solvent in any of the reactions (i) and (ii). The reaction time ranges from 1 to 24 hours for each reaction.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound can be obtained.

The compound (V) can be produced by reacting a compound represented by the formula (VIII)

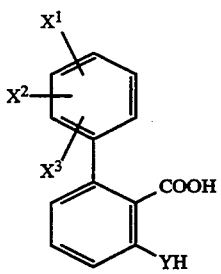

(VIII)

wherein $X^1$, $X^2$, $X^3$ and Y are as defined above, with an acid-halogenating agent or an active esterifying agent (hereinafter reaction (iii)), and reacting the resulting reaction product with the compound derivative represented by the formula (VI) (hereinafter reaction (iv)).

The above reactions (iii) and (iv) can be carried out according to the foregoing reactions (i) and (ii), respectively.

The compounds represented by the formula (II) and (VII) can be produced according to SYNTHESIS, 1980, 814, CHEMISTRY LETTERS, 1990, 143, CHEMISTRY LETTERS, 1990, 807, SYNTHESIS, 1992, 413, Japanese Patent Applications KOKAI Nos. 2-108674, 4-112876, EP 402751, WO91-13065, etc.

The present compounds (I) include their stereoisomers having a herbicidal activity.

The present compounds (I) have excellent herbicidal activity and some of them have excellent selectivity between crops and weeds.

That is, the present compounds, when used for foliar treatment and soil treatment in upland fields, ridge or no-cultivating area, exhibit herbicidal activity against various weeds, such as, Polygonaceae
  wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*)
Portulacaceae
  common purslane (*Portulaca oleracea*)
Caryophyllaceae
  common chickweed (*Stellaria media*)
Chenopodiaceae
  common lambsquarters (*Chenopodium album*), kochia (*Kochia scoparia*)
Amaranthaceae
  redroot pigweed (*Amaranthus retroflexus*), smooth pigweed (*Amaranthus hybridus*)
Cruciferae
  wild radish (*Raphanus raphanistrum*), wild mustard (*Brassica kaber*), shepherdspurse (*Capsella bursapastoris*)
Leguminosae
  hemp sesbania (*Sesbania exaltata*), sicklepod (*Cassia obtusifolia*), Florida beggarweed (*Desmodium tortuosum*), white clover (*Trifolium repens*)
Malvaceae
  velvetleaf (*Abutilon theophrasti*), prickly sida (*Sida spinosa*)
Violaceae
  field pansy (*Viola arvensis*), wild pansy (*Viola tricolor*)
Rubiaceae
  catchweed bedstraw (*Galium aparine*)
Convolvulaceae
  ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiatae
  red deadnettle (*Lamium purpureum*), henbit (*Lamium amplexicaule*)
Solanaceae
  jimsonweed (*Datula stramonium*), black nightshade (*Solanum nigram*)
Scrophulariaceae
  birdseye speedwell (*Veronica persica*), ivyleaf speedwell (*Veronica hederaefolia*)
Compositae
  common cocklebur (*Xanthium pensylvanicum*), common sunflower (*Helianthus annuus*), scentless chamomile (*Matricaria inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*)
Boraginaceae
  field forget-me-not (*Myosotis arvensis*)
Asclepiadaceae
  common milkweed (*Asclepias syriaca*)
Euphorbiaceae
  sun spurge (*Euphorbia helioscopia*), spotted spurge (*Euphorbia maculata*)
Gramineae
  barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopercurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)
Commelinaceae
  common dayflower (*Commelina communis*)
Equisetaceae
  field horsetail (*Equisetum arvense*), and
Cyperaceae
  rice flatsedge (*Cyperus iria*), purple nutsedge (*Cyperus rotundus*), yellow nutsedge (*Cyperus esculentus*).

In addition, some of the present compounds give such no phytotoxicity as becoming a problem to main crops such as corn (*Zea mays*), wheat (*Triticum aestivum*), barley (*Hordeum vulgare*), rice (*Oryza sativa*), soybean (*Glycine max*), cotton (*Gossypium spp*), sugar beet (*Beta vulgaris*), peanut (*Arachis hypogaea*), sunflower (*Helianthus annuus*), rape (*Brassica napus*), etc. and horticultural crops such as flower, ornamental plants and vegetables.

The present compound (I) also can safely be used for no-till cultivation in soybean fields, peanut fields, corn fields, etc., and some of them give such no phytotoxicity as becoming a problem to crops.

In flooding treatment in paddy fields, the present compounds exhibit herbicidal activity against weeds such as Gramineae
  *Echinochloa oryzicola*
Scrophulariaceae
  common falsepimpernel (*Lindernia procumbens*)
Lythraceae
  *Rotala indica, Ammannia multiflora*

Elatinaceae
 *Elatine triandra*
Cyperaceae
 smallflower umbrellaplant (*Cyperus difformis*), *Scirpus juncoides*, needle spikerush (*Eleocharis acicularis*), *Cyperus serotinus, Eleocharis kuroguwai*
Pontederiaceae
 *Monochoria vaginalis*
Alismataceae
 *Sagittaria pygmaea, Sagittaria trifolia, Alisma canaliculatum*
Potamogetonaceae
 roundleaf pondweed (*Potamogeton distinctus*), and Umbelliferae
 *Oenanthe javanica*

Some of the present compound give such no phytotoxicity as becoming a problem to transplanted rice plant or direct seeded rice plant in paddy field.

The present compound (I) can be used as an active ingredient for herbicides used in orchards, pastures, turfs, forests, afforestation area and non-agricultural fields (e.g. water way, canal), etc.

When the present compound (I) is used as an active ingredient for herbicides, it is usually formulated before use into emulsifiable concentrates, wettable powders, suspension formulations, granules, water-dispersible granules, etc. by mixing with solid carriers, liquid carriers, surface active agents or other auxiliaries for formulation.

The content of the compound (I) as an active ingredient in these preparations is normally within a range of about 0.002 to 90% by weight, preferably of about 0.003 to 80% by weight.

Examples of the solid carriers are fine powders or granules of kaolin clay, attapulgite clay, bentonite, terra alba, pyrophyllite, talc, diatomaceous earth, calcite, walnut shell powders, urea, ammonium sulfate, synthetic hydrated silicon dioxide, etc.

Examples of the liquid carriers are aromatic hydrocarbons (e.g. xylene, alkylbenzene, methylnaphthalene, phenylquinolylethane), alcohols (e.g. isopropanol, ethylene glycol), esters (e.g. dialkyl phthalate), ketones (e.g. acetone, cyclohexanone, isophorone), mineral oils (e.g. machine oil), vegetable oils (e.g. soybean oil, cotton seed oil), dimethyl sulfoxide, N,N-dimethylformamide, acetonitrile, N-methylpyrrolidone, water, etc.

Examples of the surface active agents used for emulsification, dispersion or spreading, etc. are anionic surface active agents such as salts of alkyl sulfates, alkylsulfonates, alkylarylsulfonates, dialkyl sulfosuccinates, salts of polyoxyethylene alkylaryl ether phosphoric acid esters, etc., and nonionic surface active agents such as polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc.

Examples of other auxiliary agents for formulation are lignosulfonates, alginates, polyvinyl alcohol, gum arabic, CMC (carboxymethyl cellulose), PAP (isopropyl acid phosphate), etc.

The present compound (I) is usually formulated and used in soil treatment, foliar treatment or flooding treatment before or after emergence of weeds. The soil treatment includes soil surface treatment, soil incorporation treatment, etc. The foliar treatment includes, in addition to treatment of plants from above, directed treatment in which treatment is limited to weeds only so as not to adhere to crops.

Build-up of the herbicidal activity of the present compound (I) can be expected by using them in mixture with other herbicides. Further, the present compound (I) can also be used in mixture with insecticides, acaricides, nematocides, fungicides, bacteriocides, plant growth regulators, fertilizers, soil improvers, etc.

When the present compound (I) is used as an active ingredient for herbicides, their dosage rate varies with weather conditions, preparation forms, when, how and where the treatment is carried out, weeds species to be controlled, crops species to be protected, etc. Usually, however, the dosage rate is from 0.5 gram to 10000 grams of the active ingredient per hectare, preferably from 1 gram to 8000 grams of the active ingredient per hectare.

The herbicidal composition of the present invention formulated into the form of an emulsifiable concentrate, a wettable powder, a suspension formulation or water dispersible granules may ordinarily be employed by diluting it with water at a volume of about 10 to 1000 liters per hectare (if necessary, adjuvants such as a spreading agent are added to the water). The granules and some suspension formulations are usually applied without being diluted.

The adjuvants include, in addition to the foregoing surface active agents, substances such as polyoxyethylene resin acids (esters), lignosulfonates, abietates, dinaphthylmethanedisulfonates and vegetable oils (e.g. crop oil concentrate, soybean oil, corn oil, cotton seed oil, sunflower oil).

The present invention will be illustrated in more detail with reference to the following production examples, formulation examples and test examples, which are not however to be interpreted as limiting the invention thereto.

First, production examples for the present compound (I) are shown.

PRODUCTION EXAMPLE 1

To 10.3 Grams of benzyl 2-(2,6-dimethoxypyrimidine-4-yloxy)-6-phenylbenzoate dissolved in 100 ml of ethyl acetate was added 0.5 g of 10% palladium on activated carbon (water content: about 50%) and the resulting mixture was subjected to catalytic reduction at room temperature under normal pressure (hydrogen pressure) for 3 hours. The palladium on carbon was filtered off and the filtrate obtained was concentrated under reduced pressure to obtain 2-(2,6-dimethoxypyrimidine-4-yloxy)-6-phenylbenzoic acid (the present compound (1)) in quantitative yield.

$^1$H-NMR (CDCl$_3$/acetone-d$_6$): δ3.87 (s, 3H) 3.96 (s, 3H) 5.84 (s, 1H) 7.15~7.62 (m, 8H)

PRODUCTION EXAMPLE 2

0.072 Gram of 60% sodium hydride in oil was washed with hexane and 5 ml of tetrahydrofuran was added thereto. Then, 0.63 g of 2-(2,6-dimethoxypyrimidine-4-yloxy)- 6-phenylbenzoic acid in 5 ml of tetrahydrofuran was added dropwise. After stirring the mixture at room temperature for 1 hour, the solvent was removed under reduced pressure to obtain sodium 2-(2,6-dimethoxypyrimidine-4-yloxy)-6-phenylbenzoate (the present compound (2)).

PRODUCTION EXAMPLE 3

Following the same procedure as in Production Example 1, 2-(2,6-dimethoxypyrimidine-4-ylthio)-6-phenylbenzoic acid can be obtained by using benzyl 2-(2,6-dimethoxypyrimidine-4-ylthio)-6-phenylbenzoate as a starting material, instead of benzyl 2-(2,6-dimethoxypyrimidine-4-yloxy)-6-phenylbenzoate.

PRODUCTION EXAMPLE 4

1.06 Grams of 2-(2,4-dimethoxypyrimidine-6-yloxy)-6-phenylbenzoic acid was suspended in 20 ml of N,N-dimethylformamide and 1.36 g of 2,4,6-triisopropylbenzenesulfonyl chloride was added thereto. After the resulting suspension was stirred at room temperature for 10 minutes, 0.82 g of 1-methylimidazole was added thereto. After stirring the resulting solution mixture at room temperature for 30 minutes, 0.4 g of N,N-diethylhydroxylamine dissolved in 1 ml of N,N-dimethylformamide was added thereto. After stirring the resulting solution mixture at room temperature for 1 hour, the reaction solution was poured into water and extracted with ethyl acetate. The organic layer separated from the aqueous layer was washed with water and dried over anhydrous magnesium sulfate. The solvent was removed under reduced pressure, and the residue obtained was subjected to thin-layer chromatography (silica gel; ethyl acetate/hexane 1:1 (V/V)) to obtain 1.05 g of 2,6-dimethoxy-4-{2-(N,N-diethylaminooxycarbonyl)-3-phenyl)phenoxy]pyrimidine (the present compound (236)).

$^1$H-NMR (CDCl$_3$) δ:0.81 (t, 6H, J=7.0 Hz) 2.65 (q, 4H, J=7.0 Hz) 3.84 (s, 3H) 3.91 (s, 3H) 5.81 (s, 1H) 7.10~7.62 (m, 8H)

PRODUCTION EXAMPLE 5

Following the same procedure as in Production Example 4, 4-{2-(N,N-diethylaminooxycarbonyl)-3-phenyl phenylthio}-2,6-dimethoxypyrimidine can be obtained by using 2-(2,4-dimethoxypyrimidine-6-ylthio)-6-phenylbenzoic acid in place of 2-(2,6-dimethoxypyrimidine-4-yloxy)-6-phenylbenzoic acid.

Tables 1 and 2 illustrate examples of the compound (I) which can be produced by the above procedure of Production Examples 1–3 and 4–5, respectively.

TABLE 1

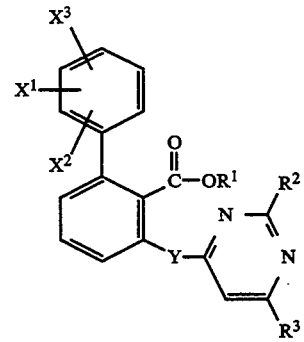

| Compound No. | X$^1$ | X$^2$ | X$^3$ | R$^1$ | Y | R$^2$ | R$^3$ | Physical properties |
|---|---|---|---|---|---|---|---|---|
| (1) | H | H | H | H | O | OCH$_3$ | OCH$_3$ | m.p. 159.4° C. |
| (2) | H | H | H | Na | O | OCH$_3$ | OCH$_3$ | m.p. 223.5° C. (decomposition) |
| (3) | H | H | H | K | O | OCH$_3$ | OCH$_3$ | m.p. 235.4° C. (decomposition) |
| (4) | H | H | H | ½Ca | O | OCH$_3$ | OCH$_3$ | |
| (5) | H | H | H | NH$_4$ | O | OCH$_3$ | OCH$_3$ | |
| (6) | H | H | H | H$_3$NCH$_3$ | O | OCH$_3$ | OCH$_3$ | |
| (7) | H | H | H | H$_3$NC$_2$H$_5$ | O | OCH$_3$ | OCH$_3$ | |
| (8) | H | H | H | H$_3$NC$_3$H$_7$(n) | O | OCH$_3$ | OCH$_3$ | |
| (9) | H | H | H | H$_3$NC$_3$H$_7$(i) | O | OCH$_3$ | OCH$_3$ | m.p. 172.5° C. |
| (10) | H | H | H | H$_3$NC$_4$H$_9$(n) | O | OCH$_3$ | OCH$_3$ | |
| (11) | H | H | H | H$_3$NC$_6$H$_{13}$(n) | O | OCH$_3$ | OCH$_3$ | |
| (12) | H | H | H | H | S | OCH$_3$ | OCH$_3$ | |
| (13) | H | H | H | Na | S | OCH$_3$ | OCH$_3$ | |
| (14) | H | H | H | K | S | OCH$_3$ | OCH$_3$ | |
| (15) | H | H | H | H$_3$NC$_3$H$_7$(i) | S | OCH$_3$ | OCH$_3$ | |
| (16) | H | H | H | H | S | OCH$_3$ | OC$_2$H$_5$ | |
| (17) | H | H | H | H | O | CH$_3$ | CH$_3$ | |
| (18) | H | H | H | H | O | CH$_3$ | OCH$_3$ | |
| (19) | H | H | H | H | O | Cl | Cl | |
| (20) | H | H | H | H | O | Cl | OCH$_3$ | |
| (21) | H | H | H | H | O | OCH$_3$ | OC$_2$H$_5$ | |
| (22) | H | H | H | H | O | OC$_2$H$_5$ | OC$_2$H$_5$ | |
| (23) | H | H | H | H | O | OC$_3$H$_7$(i) | OC$_3$H$_7$(i) | |
| (24) | 2-CH$_3$ | H | H | H | O | OCH$_3$ | OCH$_3$ | resinous |
| (25) | 2-CH$_3$ | H | H | Na | O | OCH$_3$ | OCH$_3$ | |
| (26) | 2-CH$_3$ | H | H | K | O | OCH$_3$ | OCH$_3$ | |
| (27) | 2-CH$_3$ | H | H | ½Ca | O | OCH$_3$ | OCH$_3$ | |
| (28) | 2-CH$_3$ | H | H | H$_3$NC$_3$H$_7$(i) | O | OCH$_3$ | OCH$_3$ | |
| (29) | 3-CH$_3$ | H | H | H | O | OCH$_3$ | OCH$_3$ | resinous |
| (30) | 3-CH$_3$ | H | H | Na | O | OCH$_3$ | OCH$_3$ | |
| (31) | 3-CH$_3$ | H | H | K | O | OCH$_3$ | OCH$_3$ | |
| (32) | 3-CH$_3$ | H | H | ½Ca | O | OCH$_3$ | OCH$_3$ | |
| (33) | 3-CH$_3$ | H | H | H$_3$NC$_3$H$_7$(i) | O | OCH$_3$ | OCH$_3$ | |
| (34) | 4-CH$_3$ | H | H | H | O | OCH$_3$ | OCH$_3$ | resinous |
| (35) | 4-CH$_3$ | H | H | Na | O | OCH$_3$ | OCH$_3$ | |
| (36) | 4-CH$_3$ | H | H | K | O | OCH$_3$ | OCH$_3$ | |

TABLE 1-continued

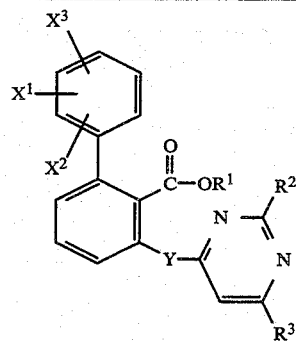

| Compound No. | $X^1$ | $X^2$ | $X^3$ | $R^1$ | Y | $R^2$ | $R^3$ | Physical properties |
|---|---|---|---|---|---|---|---|---|
| (37) | 4-$CH_3$ | H | H | ½Ca | O | $OCH_3$ | $OCH_3$ | |
| (38) | 4-$CH_3$ | H | H | $H_3NC_3H_7(i)$ | O | $OCH_3$ | $OCH_3$ | |
| (39) | 2-F | H | H | H | O | $OCH_3$ | $OCH_3$ | |
| (40) | 2-F | H | H | Na | O | $OCH_3$ | $OCH_3$ | |
| (41) | 2-F | H | H | K | O | $OCH_3$ | $OCH_3$ | |
| (42) | 2-F | H | H | ½Ca | O | $OCH_3$ | $OCH_3$ | |
| (43) | 2-F | H | H | $H_3NC_3H_7(i)$ | O | $OCH_3$ | $OCH_3$ | |
| (44) | 3-F | H | H | H | O | $OCH_3$ | $OCH_3$ | |
| (45) | 3-F | H | H | Na | O | $OCH_3$ | $OCH_3$ | |
| (46) | 3-F | H | H | K | O | $OCH_3$ | $OCH_3$ | |
| (47) | 3-F | H | H | ½Ca | O | $OCH_3$ | $OCH_3$ | |
| (48) | 3-F | H | H | $H_3NC_3H_7(i)$ | O | $OCH_3$ | $OCH_3$ | |
| (49) | 4-F | H | H | H | O | $OCH_3$ | $OCH_3$ | |
| (50) | 4-F | H | H | Na | O | $OCH_3$ | $OCH_3$ | |
| (51) | 4-F | H | H | K | O | $OCH_3$ | $OCH_3$ | |
| (52) | 4-F | H | H | ½Ca | O | $OCH_3$ | $OCH_3$ | |
| (53) | 4-F | H | H | $H_3NC_3H_7(i)$ | O | $OCH_3$ | $OCH_3$ | |
| (54) | 2-Cl | H | H | H | O | $OCH_3$ | $OCH_3$ | |
| (55) | 2-Cl | H | H | Na | O | $OCH_3$ | $OCH_3$ | |
| (56) | 2-Cl | H | H | K | O | $OCH_3$ | $OCH_3$ | |
| (57) | 2-Cl | H | H | ½Ca | O | $OCH_3$ | $OCH_3$ | |
| (58) | 2-Cl | H | H | $H_3NC_3H_7(i)$ | O | $OCH_3$ | $OCH_3$ | |
| (59) | 3-Cl | H | H | H | O | $OCH_3$ | $OCH_3$ | m.p. 137.1° C. |
| (60) | 3-Cl | H | H | Na | O | $OCH_3$ | $OCH_3$ | |
| (61) | 3-Cl | H | H | K | O | $OCH_3$ | $OCH_3$ | |
| (62) | 3-Cl | H | H | ½Ca | O | $OCH_3$ | $OCH_3$ | |
| (63) | 3-Cl | H | H | $H_3NC_3H_7(i)$ | O | $OCH_3$ | $OCH_3$ | |
| (64) | 4-Cl | H | H | H | O | $OCH_3$ | $OCH_3$ | |
| (65) | 4-Cl | H | H | Na | O | $OCH_3$ | $OCH_3$ | |
| (66) | 4-Cl | H | H | K | O | $OCH_3$ | $OCH_3$ | |
| (67) | 4-Cl | H | H | ½Ca | O | $OCH_3$ | $OCH_3$ | |
| (68) | 4-Cl | H | H | $H_3NC_3H_7(i)$ | O | $OCH_3$ | $OCH_3$ | |
| (69) | 2-Br | H | H | H | O | $OCH_3$ | $OCH_3$ | |
| (70) | 2-Br | H | H | Na | O | $OCH_3$ | $OCH_3$ | |
| (71) | 2-Br | H | H | K | O | $OCH_3$ | $OCH_3$ | |
| (72) | 2-Br | H | H | ½Ca | O | $OCH_3$ | $OCH_3$ | |
| (73) | 2-Br | H | H | $H_3NC_3H_7(i)$ | O | $OCH_3$ | $OCH_3$ | |
| (74) | 3-Br | H | H | H | O | $OCH_3$ | $OCH_3$ | |
| (75) | 3-Br | H | H | Na | O | $OCH_3$ | $OCH_3$ | |
| (76) | 3-Br | H | H | K | O | $OCH_3$ | $OCH_3$ | |
| (77) | 3-Br | H | H | ½Ca | O | $OCH_3$ | $OCH_3$ | |
| (78) | 3-Br | H | H | $H_3NC_3H_7(i)$ | O | $OCH_3$ | $OCH_3$ | |
| (79) | 4-Br | H | H | H | O | $OCH_3$ | $OCH_3$ | |
| (80) | 4-Br | H | H | Na | O | $OCH_3$ | $OCH_3$ | |
| (81) | 4-Br | H | H | K | O | $OCH_3$ | $OCH_3$ | |
| (82) | 4-Br | H | H | ½Ca | O | $OCH_3$ | $OCH_3$ | |
| (83) | 4-Br | H | H | $H_3NC_3H_7(i)$ | O | $OCH_3$ | $OCH_3$ | |
| (84) | 2-$OCH_3$ | H | H | H | O | $OCH_3$ | $OCH_3$ | m.p. 59.1° C. |
| (85) | 2-$OCH_3$ | H | H | Na | O | $OCH_3$ | $OCH_3$ | |
| (87) | 2-$OCH_3$ | H | H | K | O | $OCH_3$ | $OCH_3$ | |
| (88) | 2-$OCH_3$ | H | H | ½Ca | O | $OCH_3$ | $OCH_3$ | |
| (89) | 2-$OCH_3$ | H | H | $H_3NC_3H_7(i)$ | O | $OCH_3$ | $OCH_3$ | |
| (90) | 3-$OCH_3$ | H | H | H | O | $OCH_3$ | $OCH_3$ | |
| (91) | 3-$OCH_3$ | H | H | Na | O | $OCH_3$ | $OCH_3$ | |
| (92) | 3-$OCH_3$ | H | H | K | O | $OCH_3$ | $OCH_3$ | |
| (93) | 3-$OCH_3$ | H | H | ½Ca | O | $OCH_3$ | $OCH_3$ | |
| (94) | 3-$OCH_3$ | H | H | $H_3NC_3H_7(i)$ | O | $OCH_3$ | $OCH_3$ | |
| (95) | 4-$OCH_3$ | H | H | H | O | $OCH_3$ | $OCH_3$ | |
| (96) | 4-$OCH_3$ | H | H | Na | O | $OCH_3$ | $OCH_3$ | |
| (97) | 4-$OCH_3$ | H | H | K | O | $OCH_3$ | $OCH_3$ | |
| (98) | 4-$OCH_3$ | H | H | ½Ca | O | $OCH_3$ | $OCH_3$ | |
| (99) | 4-$OCH_3$ | H | H | $H_3NC_3H_7(i)$ | O | $OCH_3$ | $OCH_3$ | |
| (100) | 2-$C_2H_5$ | H | H | H | O | $OCH_3$ | $OCH_3$ | |

TABLE 1-continued

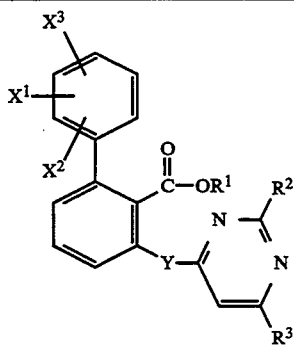

| Compound No. | $X^1$ | $X^2$ | $X^3$ | $R^1$ | Y | $R^2$ | $R^3$ | Physical properties |
|---|---|---|---|---|---|---|---|---|
| (101) | 2-$C_2H_5$ | H | H | Na | O | $OCH_3$ | $OCH_3$ | |
| (102) | 2-$C_2H_5$ | H | H | K | O | $OCH_3$ | $OCH_3$ | |
| (103) | 2-$C_2H_5$ | H | H | ½Ca | O | $OCH_3$ | $OCH_3$ | |
| (104) | 2-$C_2H_5$ | H | H | $H_3NC_3H_7(i)$ | O | $OCH_3$ | $OCH_3$ | |
| (105) | 3-$C_3H_7$(n) | H | H | H | O | $OCH_3$ | $OCH_3$ | |
| (106) | 3-$C_3H_7$(n) | H | H | Na | O | $OCH_3$ | $OCH_3$ | |
| (107) | 3-$C_3H_7$(n) | H | H | K | O | $OCH_3$ | $OCH_3$ | |
| (108) | 3-$C_3H_7$(n) | H | H | ½Ca | O | $OCH_3$ | $OCH_3$ | |
| (109) | 3-$C_3H_7$(n) | H | H | $H_3NC_3H_7(i)$ | O | $OCH_3$ | $OCH_3$ | |
| (110) | 4-$C_4H_9$(n) | H | H | H | O | $OCH_3$ | $OCH_3$ | |
| (111) | 4-$C_4H_9$(n) | H | H | Na | O | $OCH_3$ | $OCH_3$ | |
| (112) | 4-$C_4H_9$(n) | H | H | K | O | $OCH_3$ | $OCH_3$ | |
| (113) | 4-$C_4H_9$(n) | H | H | ½Ca | O | $OCH_3$ | $OCH_3$ | |
| (114) | 4-$C_4H_9$(n) | H | H | $H_3NC_3H_7(i)$ | O | $OCH_3$ | $OCH_3$ | |
| (115) | 2-$OC_2H_5$ | H | H | H | O | $OCH_3$ | $OCH_3$ | |
| (116) | 2-$OC_2H_5$ | H | H | Na | O | $OCH_3$ | $OCH_3$ | |
| (117) | 2-$OC_2H_5$ | H | H | K | O | $OCH_3$ | $OCH_3$ | |
| (118) | 2-$OC_2H_5$ | H | H | ½Ca | O | $OCH_3$ | $OCH_3$ | |
| (119) | 2-$OC_2H_5$ | H | H | $H_3NC_3H_7(i)$ | O | $OCH_3$ | $OCH_3$ | |
| (120) | 3-$OC_3H_7$(i) | H | H | H | O | $OCH_3$ | $OCH_3$ | |
| (121) | 3-$OC_3H_7$(i) | H | H | Na | O | $OCH_3$ | $OCH_3$ | |
| (122) | 3-$OC_3H_7$(i) | H | H | K | O | $OCH_3$ | $OCH_3$ | |
| (123) | 3-$OC_3H_7$(i) | H | H | ½Ca | O | $OCH_3$ | $OCH_3$ | |
| (124) | 3-$OC_3H_7$(i) | H | H | $H_3NC_3H_7(i)$ | O | $OCH_3$ | $OCH_3$ | |
| (125) | 4-$OC_4H_9$(n) | H | H | H | O | $OCH_3$ | $OCH_3$ | |
| (126) | 4-$OC_4H_9$(n) | H | H | Na | O | $OCH_3$ | $OCH_3$ | |
| (127) | 4-$OC_4H_9$(n) | H | H | K | O | $OCH_3$ | $OCH_3$ | |
| (128) | 4-$OC_4H_9$(n) | H | H | ½Ca | O | $OCH_3$ | $OCH_3$ | |
| (129) | 4-$OC_4H_9$(n) | H | H | $H_3NC_3H_7(i)$ | O | $OCH_3$ | $OCH_3$ | |
| (130) | 2-F | 4-F | H | H | O | $OCH_3$ | $OCH_3$ | |
| (131) | 2-F | 4-F | H | Na | O | $OCH_3$ | $OCH_3$ | |
| (132) | 2-F | 4-F | H | K | O | $OCH_3$ | $OCH_3$ | |
| (133) | 2-F | 4-F | H | ½Ca | O | $OCH_3$ | $OCH_3$ | |
| (134) | 2-F | 4-F | H | $H_3NC_3H_7(i)$ | O | $OCH_3$ | $OCH_3$ | |
| (135) | 2-Cl | 4-Cl | H | H | O | $OCH_3$ | $OCH_3$ | |
| (136) | 2-Cl | 4-Cl | H | Na | O | $OCH_3$ | $OCH_3$ | |
| (137) | 2-Cl | 4-Cl | H | K | O | $OCH_3$ | $OCH_3$ | |
| (138) | 2-Cl | 4-Cl | H | ½Ca | O | $OCH_3$ | $OCH_3$ | |
| (139) | 2-Cl | 4-Cl | H | $H_3NC_3H_7(i)$ | O | $OCH_3$ | $OCH_3$ | |
| (140) | 2-F | 6-F | H | H | O | $OCH_3$ | $OCH_3$ | m.p. 53.5° C. |
| (141) | 2-F | 6-F | H | Na | O | $OCH_3$ | $OCH_3$ | |
| (142) | 2-F | 6-F | H | K | O | $OCH_3$ | $OCH_3$ | |
| (143) | 2-F | 6-F | H | ½Ca | O | $OCH_3$ | $OCH_3$ | |
| (144) | 2-F | 6-F | H | $H_3NC_3H_7(i)$ | O | $OCH_3$ | $OCH_3$ | |
| (145) | 2-Cl | 6-Cl | H | H | O | $OCH_3$ | $OCH_3$ | |
| (146) | 2-Cl | 6-Cl | H | Na | O | $OCH_3$ | $OCH_3$ | |
| (147) | 2-Cl | 6-Cl | H | K | O | $OCH_3$ | $OCH_3$ | |
| (148) | 2-Cl | 6-Cl | H | ½Ca | O | $OCH_3$ | $OCH_3$ | |
| (149) | 2-Cl | 6-Cl | H | $H_3NC_3H_7(i)$ | O | $OCH_3$ | $OCH_3$ | |
| (150) | 2-Cl | 4-F | H | H | O | $OCH_3$ | $OCH_3$ | |
| (151) | 2-Cl | 4-F | H | Na | O | $OCH_3$ | $OCH_3$ | |
| (152) | 2-Cl | 4-F | H | K | O | $OCH_3$ | $OCH_3$ | |
| (153) | 2-Cl | 4-F | H | ½Ca | O | $OCH_3$ | $OCH_3$ | |
| (154) | 2-Cl | 4-F | H | $H_3NC_3H_7(i)$ | O | $OCH_3$ | $OCH_3$ | |
| (155) | 2-Cl | 6-F | H | H | O | $OCH_3$ | $OCH_3$ | |
| (156) | 2-Cl | 6-F | H | Na | O | $OCH_3$ | $OCH_3$ | |
| (157) | 2-Cl | 6-F | H | K | O | $OCH_3$ | $OCH_3$ | |
| (158) | 2-Cl | 6-F | H | ½Ca | O | $OCH_3$ | $OCH_3$ | |
| (159) | 2-Cl | 6-F | H | $H_3NC_3H_7(i)$ | O | $OCH_3$ | $OCH_3$ | |
| (160) | 3-Cl | 5-Cl | H | H | O | $OCH_3$ | $OCH_3$ | |
| (161) | 3-Cl | 5-Cl | H | Na | O | $OCH_3$ | $OCH_3$ | |
| (162) | 3-Cl | 5-Cl | H | K | O | $OCH_3$ | $OCH_3$ | |
| (163) | 3-Cl | 5-Cl | H | ½Ca | O | $OCH_3$ | $OCH_3$ | |

TABLE 1-continued

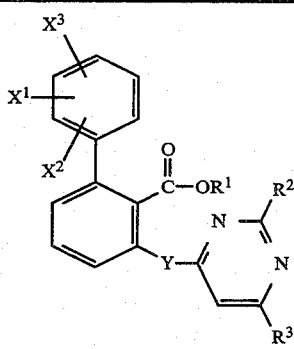

| Compound No. | X¹ | X² | X³ | R¹ | Y | R² | R³ | Physical properties |
|---|---|---|---|---|---|---|---|---|
| (164) | 3-Cl | 5-Cl | H | H₃NC₃H₇(i) | O | OCH₃ | OCH₃ | |
| (165) | 4-Cl | 2-OCH₃ | H | H | O | OCH₃ | OCH₃ | |
| (166) | 4-Cl | 2-OCH₃ | H | Na | O | OCH₃ | OCH₃ | |
| (167) | 4-Cl | 2-OCH₃ | H | K | O | OCH₃ | OCH₃ | |
| (168) | 4-Cl | 2-OCH₃ | H | ½Ca | O | OCH₃ | OCH₃ | |
| (169) | 4-Cl | 2-OCH₃ | H | H₃NC₃H₇(i) | O | OCH₃ | OCH₃ | |
| (170) | 2-Cl | 4-Cl | 6-Cl | 6-Cl | O | OCH₃ | OCH₃ | |
| (171) | 2-Cl | 4-Cl | 6-Cl | Na | O | OCH₃ | OCH₃ | |
| (172) | 2-Cl | 4-Cl | 6-Cl | K | O | OCH₃ | OCH₃ | |
| (173) | 2-Cl | 4-Cl | 6-Cl | ½Ca | O | OCH₃ | OCH₃ | |
| (174) | 2-Cl | 4-Cl | 6-Cl | H₃NC₃H₇(i) | O | OCH₃ | OCH₃ | |
| (175) | 2-NO₂ | H | H | H | O | OCH₃ | OCH₃ | |
| (176) | 2-Cl | 4-NO₂ | H | H | O | OCH₃ | OCH₃ | |
| (177) | 2-CH₃ | 3-NO₂ | 6-F | H | O | OCH₃ | OCH₃ | |
| (178) | 3-NO₂ | H | H | K | O | OCH₃ | OCH₃ | |
| (179) | 4-NO₂ | H | H | Na | O | OCH₃ | OCH₃ | |
| (180) | 2-CN | H | H | H | O | OCH₃ | OCH₃ | |
| (181) | 3-CN | H | H | H | O | OCH₃ | OCH₃ | |
| (182) | 4-CN | H | H | ½Ca | O | OCH₃ | OCH₃ | |
| (183) | 2-CH₃ | 4-Br | 6-CN | H₂NC₃H₇(i) | S | OCH₃ | OCH₃ | |
| (184) | H | H | H | H | O | Cl | SCH₃ | |
| (185) | 2-F | H | H | Na | O | Cl | SCH₃ | |
| (186) | 3-Cl | H | H | H | O | SCH₃ | SCH₃ | |
| (187) | H | H | H | H | O | CH₃ | SCH₃ | |
| (188) | H | H | H | H | O | OCH₃ | SCH₃ | |
| (189) | H | H | H | H | O | OCHF₂ | OCHF₂ | |
| (190) | H | H | H | H | O | OCH₃ | OCF₃ | |
| (191) | 2-OH | H | H | H | O | OCH₃ | OCH₃ | $n_D^{24}$ 1.5791 |
| (192) | 3-OH | H | H | Na | O | OCH₃ | OCH₃ | |
| (193) | 4-OH | H | H | K | O | OCH₃ | OCH₃ | |
| (194) | 2-Cl | 3-Cl | 5-Cl | H | O | OCH₃ | OCH₃ | |
| (195) | 2-Cl | 3-Cl | 5-Cl | Na | O | OCH₃ | OCH₃ | |
| (196) | 2-Cl | 3-Cl | 5-Cl | K | O | OCH₃ | OCH₃ | |
| (197) | 2-Cl | 3-Cl | 5-Cl | ½Ca | O | OCH₃ | OCH₃ | |
| (198) | 2-Cl | 3-Cl | 5-Cl | H₃NC₃H₇(i) | O | OCH₃ | OCH₃ | |
| (199) | 2-CH₃ | 4-CH₃ | 6-CH₃ | H | O | OCH₃ | OCH₃ | m.p. 143.4° C. |
| (200) | 2-CH₃ | 4-CH₃ | 6-CH₃ | Na | O | OCH₃ | OCH₃ | |
| (201) | 2-CH₃ | 4-CH₃ | 6-CH₃ | K | O | OCH₃ | OCH₃ | |
| (202) | 2-CH₃ | 4-CH₃ | 6-CH₃ | ½Ca | O | OCH₃ | OCH₃ | |
| (203) | 2-CH₃ | 4-CH₃ | 6-CH₃ | H₃NC₃H₇(i) | O | OCH₃ | OCH₃ | |
| (204) | 2-CH₃ | 3-CH₃ | 4-OCH₃ | H | O | OCH₃ | OCH₃ | |
| (205) | 2-CH₃ | 3-CH₃ | 4-OCH₃ | Na | O | OCH₃ | OCH₃ | |
| (206) | 2-CH₃ | 3-CH₃ | 4-OCH₃ | K | O | OCH₃ | OCH₃ | |
| (207) | 2-CH₃ | 3-CH₃ | 4-OCH₃ | ½Ca | O | OCH₃ | OCH₃ | |
| (208) | 2-CH₃ | 3-CH₃ | 4-OCH₃ | H₃NC₃H₇(i) | O | OCH₃ | OCH₃ | |
| (476) | 2-CF₃ | H | H | H | " | " | " | |
| (477) | 3-CF₃ | " | " | " | " | " | " | |
| (478) | 4-CF₃ | " | " | " | " | " | " | |
| (479) | 2-CF₃ | " | " | Na | " | " | " | |

TABLE 2

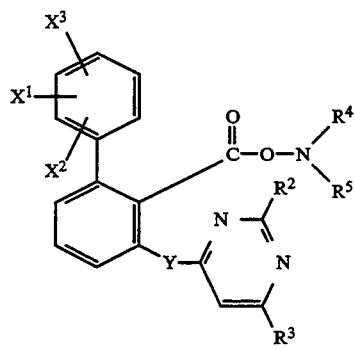

| Compound No. | $X^1$ | $X^2$ | $X^3$ | Y | $R^2$ | $R^3$ | $R^4$ | $R^5$ | Physical properties |
|---|---|---|---|---|---|---|---|---|---|
| (209) | H | H | H | O | OCH$_3$ | OCH$_3$ | H | CH$_3$ | |
| (210) | " | " | " | " | " | " | " | C$_2$H$_5$ | |
| (211) | " | " | " | " | " | " | " | C$_3$H$_7$(n) | |
| (212) | " | " | " | " | " | " | " | C$_4$H$_9$(t) | |
| (213) | " | " | " | " | " | " | " | cyclopentyl | |
| (214) | H | H | H | O | OCH$_3$ | OCH$_3$ | H | cyclohexyl | |
| (215) | " | " | " | " | " | " | " | C$_6$H$_5$ | |
| (216) | " | " | " | " | " | " | " | CH$_2$—C$_6$H$_5$ | |
| (217) | " | " | " | " | " | " | CH$_3$ | CH$_3$ | m.p. 127.3° C. (decomposition) |
| (218) | " | " | " | " | " | " | " | C$_2$H$_5$ | |
| (219) | " | " | " | " | " | " | " | C$_3$H$_7$(n) | |
| (220) | " | " | " | " | " | " | " | C$_4$H$_9$(n) | |
| (221) | " | " | " | " | " | " | " | cyclopentyl | |
| (222) | H | H | H | O | OCH$_3$ | OCH$_3$ | CH$_3$ | cyclohexyl | |
| (223) | " | " | " | " | " | " | " | C$_6$H$_5$ | |
| (224) | " | " | " | " | " | " | " | 2-methylphenyl | |
| (225) | " | " | " | " | " | " | " | 3-fluorophenyl | |
| (226) | " | " | " | " | " | " | " | 4-chlorophenyl | |

TABLE 2-continued

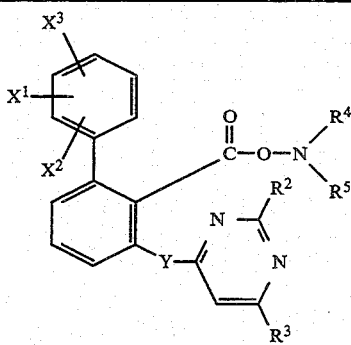

| Compound No. | $X^1$ | $X^2$ | $X^3$ | Y | $R^2$ | $R^3$ | $R^4$ | $R^5$ | Physical properties |
|---|---|---|---|---|---|---|---|---|---|
| (227) | H | H | H | O | $OCH_3$ | $OCH_3$ | $CH_3$ | 3-methoxyphenyl | |
| (228) | " | " | " | " | " | " | " | $CH_2-C_6H_5$ | |
| (229) | " | " | " | " | " | " | " | $CH_2$-(3-methylphenyl) | |
| (230) | " | " | " | " | " | " | " | $CH_2$-(2-chlorophenyl) | |
| (231) | " | " | " | " | " | " | " | $CH_2$-(4-fluorophenyl) | |
| (232) | H | H | H | O | $OCH_3$ | $OCH_3$ | $CH_3$ | $CH_2$-(4-methoxyphenyl) | |
| (233) | " | " | " | " | " | " | " | $CH_2$-(2,4-dichlorophenyl) | |
| (234) | " | " | " | " | " | " | " | $CH_2$-(2,5-dimethoxyphenyl) | |
| (235) | " | " | " | " | " | " | " | $CH_2$-(3,4-dimethylphenyl) | |
| (236) | H | H | H | O | $OCH_3$ | $OCH_3$ | $C_2H_5$ | $C_2H_5$ | $n_D^{25}$ 1.5586 |
| (237) | " | " | " | " | " | " | $C_3H_7(n)$ | $C_3H_7(n)$ | |
| (238) | " | " | " | " | " | " | $C_4H_9(n)$ | $C_4H_9(n)$ | |

TABLE 2-continued

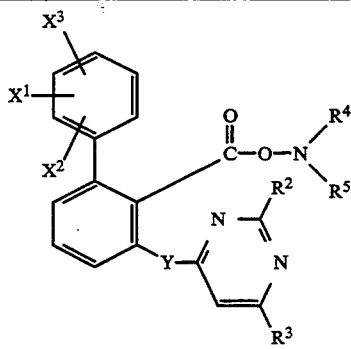

| Compound No. | X¹ | X² | X³ | Y | R² | R³ | R⁴ | R⁵ | Physical properties |
|---|---|---|---|---|---|---|---|---|---|
| (239) | " | " | " | " | " | " | cyclopentyl | cyclopentyl | |
| (240) | " | " | " | " | " | " | cyclohexyl | cyclohexyl | |
| (241) | " | " | " | " | " | " | $C_6H_5$ | $C_6H_5$ | |
| (242) | " | " | " | " | " | " | $CH_2-C_6H_5$ | $CH_2-C_6H_5$ | $n_D^{25}$ 1.5851 |
| (243) | " | " | " | S | " | " | H | $C_4H_9(t)$ | |
| (244) | " | " | " | " | " | " | " | cyclohexyl | |
| (245) | H | H | H | S | $OCH_3$ | $OCH_3$ | $CH_3$ | $CH_3$ | |
| (246) | " | " | " | " | " | " | " | $C_2H_5$ | |
| (247) | " | " | " | " | " | " | " | $C_3H_7(n)$ | |
| (248) | " | " | " | " | " | " | $C_2H_5$ | $C_2H_5$ | |
| (249) | " | " | " | " | " | " | $C_3H_7(n)$ | $C_3H_7(n)$ | |
| (250) | " | " | " | " | " | " | $C_4H_9(n)$ | $C_4H_9(n)$ | |
| (251) | " | " | " | " | " | " | $CH_3$ | $C_6H_5$ | |
| (252) | " | " | " | " | " | " | " | $CH_2-C_6H_5$ | |
| (253) | " | " | " | " | " | " | $CH_2-C_6H_5$ | " | |
| (254) | " | " | " | O | " | $OC_2H_5$ | $CH_3$ | $CH_3$ | |
| (255) | " | " | " | " | " | " | " | $C_2H_5$ | |
| (256) | " | " | " | " | " | " | $C_2H_5$ | " | |
| (257) | H | H | H | O | $OCH_3$ | $OC_2H_5$ | $C_3H_7(n)$ | $C_3H_7(n)$ | |
| (258) | " | " | " | " | " | " | $C_4H_9(n)$ | $C_4H_9(n)$ | |
| (259) | " | " | " | " | $OC_2H_5$ | $OC_2H_5$ | $CH_3$ | $CH_3$ | |
| (260) | " | " | " | " | $OC_3H_7(i)$ | $OC_3H_7(i)$ | " | " | |
| (261) | " | " | " | " | $CH_3$ | $CH_3$ | " | " | |
| (262) | " | " | " | " | $OCH_3$ | " | " | " | |
| (263) | " | " | " | " | Cl | Cl | " | " | |
| (264) | " | " | " | " | $OCH_3$ | " | " | " | |
| (265) | " | " | " | " | " | $OCH_3$ | $-(CH_2)_4-$ | | |
| (266) | " | " | " | " | " | " | $-(CH_2)_5-$ | | $n_D^{25}$ 1.5697 |
| (267) | " | " | " | " | " | " | $-(CH_2)_6-$ | | |
| (268) | H | H | H | O | $OCH_3$ | $OCH_3$ | $-CH(CH_3)-(CH_2)_3-CH(CH_3)-$ | | |
| (269) | " | " | " | " | " | " | $-(CH_2)_2-O-(CH_2)_2-$ | | |
| (270) | " | " | " | " | " | " | $-CH(CH_3)-CH_2-O-CH_2-CH(CH_3)-$ | | |
| (271) | " | " | " | " | " | " | $-CH_2-CH(CH_3)-O-CH(CH_3)-CH_2-$ | | |
| (272) | " | " | " | " | " | " | $C_5H_{11}(n)$ | $C_5H_{11}(n)$ | |
| (274) | " | " | " | " | " | " | $C_6H_{13}(n)$ | $C_6H_{13}(n)$ | |

TABLE 2-continued

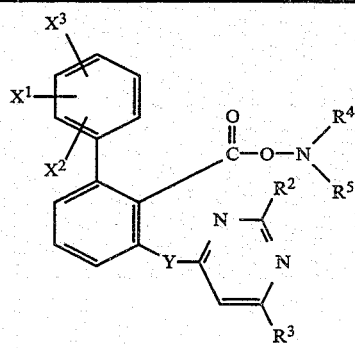

| Compound No. | X¹ | X² | X³ | Y | R² | R³ | R⁴ | R⁵ | Physical properties |
|---|---|---|---|---|---|---|---|---|---|
| (277) | 2-CH₃ | H | H | O | OCH₃ | OCH₃ | CH₃ | CH₃ | $n_D^{25}$ 1.5135 |
| (278) | " | " | " | " | " | " | " | C₂H₅ | |
| (279) | " | " | " | " | " | " | " | C₃H₇(n) | |
| (280) | " | " | " | " | " | " | C₂H₅ | C₂H₅ | |
| (281) | " | " | " | " | " | " | C₃H₇(n) | C₃H₇(n) | |
| (282) | " | " | " | " | " | " | C₄H₉(n) | C₄H₉(n) | |
| (283) | 3-CH₃ | " | " | " | " | " | CH₃ | CH₃ | $n_D^{25}$ 1.5641 |
| (284) | " | " | " | " | " | " | " | C₂H₅ | |
| (285) | " | " | " | " | " | " | " | C₃H₇(n) | |
| (286) | " | " | " | " | " | " | C₂H₅ | C₂H₅ | |
| (287) | " | " | " | " | " | " | C₃H₇(n) | C₃H₇(n) | |
| (288) | " | " | " | " | " | " | C₄H₉(n) | C₄H₉(n) | |
| (289) | 4-CH₃ | H | H | O | OCH₃ | OCH₃ | CH₃ | CH₃ | $n_D^{25}$ 1.5617 |
| (290) | " | " | " | " | " | " | " | C₂H₅ | |
| (291) | " | " | " | " | " | " | " | C₃H₇(n) | |
| (292) | " | " | " | " | " | " | C₂H₅ | C₂H₅ | |
| (293) | " | " | " | " | " | " | C₃H₇(n) | C₃H₇(n) | |
| (294) | " | " | " | " | " | " | C₄H₉(n) | C₄H₉(n) | |
| (295) | 2-F | " | " | " | " | " | CH₃ | CH₃ | |
| (296) | " | " | " | " | " | " | " | C₂H₅ | |
| (297) | " | " | " | " | " | " | " | C₃H₇(n) | |
| (298) | " | " | " | " | " | " | C₂H₅ | C₂H₅ | |
| (299) | " | " | " | " | " | " | C₃H₇(n) | C₃H₇(n) | |
| (300) | " | " | " | " | " | " | C₄H₉(n) | C₄H₉(n) | |
| (301) | 3-F | " | " | " | " | " | CH₃ | CH₃ | |
| (302) | 3-F | H | H | O | OCH₃ | OCH₃ | CH₃ | C₂H₅ | |
| (303) | " | " | " | " | " | " | " | C₃H₇(n) | |
| (304) | " | " | " | " | " | " | C₂H₅ | C₂H₅ | |
| (305) | " | " | " | " | " | " | C₃H₇(n) | C₃H₇(n) | |
| (306) | " | " | " | " | " | " | C₄H₉(n) | C₄H₉(n) | |
| (307) | 4-F | " | " | " | " | " | CH₃ | CH₃ | |
| (308) | " | " | " | " | " | " | " | C₂H₅ | |
| (309) | " | " | " | " | " | " | " | C₃H₇(n) | |
| (310) | " | " | " | " | " | " | C₂H₅ | C₂H₅ | |
| (311) | " | " | " | " | " | " | C₃H₇(n) | C₃H₇(n) | |
| (312) | " | " | " | " | " | " | C₄H₉(n) | C₄H₉(n) | |
| (313) | 2-Cl | " | " | " | " | " | CH₃ | CH₃ | |
| (314) | " | " | " | " | " | " | " | C₂H₅ | |
| (315) | 2-Cl | H | H | O | OCH₃ | OCH₃ | CH₃ | C₃H₇(n) | |
| (316) | " | " | " | " | " | " | C₂H₅ | C₂H₅ | |
| (317) | " | " | " | " | " | " | C₃H₇(n) | C₃H₇(n) | |
| (318) | " | " | " | " | " | " | C₄H₉(n) | C₄H₉(n) | |
| (319) | 3-Cl | " | " | " | " | " | CH₃ | CH₃ | $n_D^{24}$ 1.5412 |
| (320) | " | " | " | " | " | " | " | C₂H₅ | |
| (321) | " | " | " | " | " | " | " | C₃H₇(n) | |
| (322) | " | " | " | " | " | " | C₂H₅ | C₂H₅ | $n_D^{24}$ 1.5546 |
| (323) | " | " | " | " | " | " | C₃H₇(n) | C₃H₇(n) | |
| (324) | " | " | " | " | " | " | C₄H₉(n) | C₄H₉(n) | |
| (325) | 4-Cl | " | " | " | " | " | CH₃ | CH₃ | |
| (326) | " | " | " | " | " | " | " | C₂H₅ | |
| (327) | 4-Cl | H | H | O | OCH₃ | OCH₃ | CH₃ | C₃H₇(n) | |
| (328) | " | " | " | " | " | " | C₂H₅ | CH₂H₅ | |
| (329) | " | " | " | " | " | " | C₃H₇(n) | C₃H₇(n) | |
| (330) | " | " | " | " | " | " | C₄H₉(n) | C₄H₉(n) | |
| (331) | 2-Br | " | " | " | " | " | CH₃ | CH₃ | |
| (332) | " | " | " | " | " | " | " | C₂H₅ | |
| (333) | " | " | " | " | " | " | " | C₃H₇(n) | |
| (334) | " | " | " | " | " | " | C₂H₅ | C₂H₅ | |
| (335) | " | " | " | " | " | " | C₃H₇(n) | C₃H₇(n) | |
| (336) | " | " | " | " | " | " | C₄H₉(n) | C₄H₉(n) | |
| (337) | 3-Br | " | " | " | " | " | CH₃ | CH₃ | |
| (338) | " | " | " | " | " | " | " | C₂H₅ | |
| (339) | 3-Br | H | H | O | OCH₃ | OCH₃ | CH₃ | C₃H₇(n) | |

TABLE 2-continued

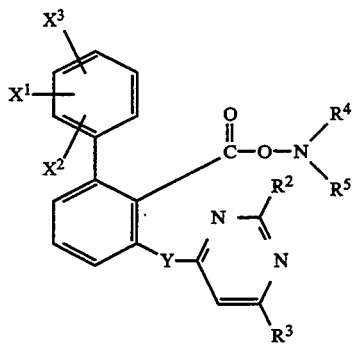

| Compound No. | $X^1$ | $X^2$ | $X^3$ | Y | $R^2$ | $R^3$ | $R^4$ | $R^5$ | Physical properties |
|---|---|---|---|---|---|---|---|---|---|
| (340) | " | " | " | " | " | " | $C_2H_5$ | $C_2H_5$ | |
| (341) | " | " | " | " | " | " | $C_3H_7(n)$ | $C_3H_7(n)$ | |
| (342) | " | " | " | " | " | " | $C_4H_9(n)$ | $C_4H_9(n)$ | |
| (343) | 4-Br | " | " | " | " | " | $CH_3$ | $CH_3$ | |
| (344) | " | " | " | " | " | " | " | $C_2H_5$ | |
| (345) | " | " | " | " | " | " | " | $C_3H_7(n)$ | |
| (346) | " | " | " | " | " | " | $C_2H_5$ | $C_2H_5$ | |
| (347) | " | " | " | " | " | " | $C_3H_7(n)$ | $C_3H_7(n)$ | |
| (348) | " | " | " | " | " | " | $C_4H_9(n)$ | $C_4H_9(n)$ | |
| (349) | 2-$OCH_3$ | " | " | " | " | " | $CH_3$ | $CH_3$ | m.p. 112.6° C. |
| (350) | " | " | " | " | " | " | " | $C_2H_5$ | |
| (351) | 2-$OCH_3$ | H | H | O | $OCH_3$ | $OCH_3$ | $CH_3$ | $C_3H_7(n)$ | |
| (352) | " | " | " | " | " | " | $C_2H_5$ | $C_2H_5$ | |
| (353) | " | " | " | " | " | " | $C_3H_7(n)$ | $C_3H_7(n)$ | |
| (354) | " | " | " | " | " | " | $C_4H_9(n)$ | $C_4H_9(n)$ | |
| (355) | 3-$OCH_3$ | " | " | " | " | " | $CH_3$ | $CH_3$ | |
| (356) | " | " | " | " | " | " | " | $C_2H_5$ | |
| (357) | " | " | " | " | " | " | " | $C_3H_7(n)$ | |
| (358) | " | " | " | " | " | " | $C_2H_5$ | $C_2H_5$ | |
| (359) | " | " | " | " | " | " | $C_3H_7(n)$ | $C_3H_7(n)$ | |
| (360) | " | " | " | " | " | " | $C_4H_9(n)$ | $C_4H_9(n)$ | |
| (361) | 4-$OCH_3$ | " | " | " | " | " | $CH_3$ | $CH_3$ | |
| (362) | " | " | " | " | " | " | " | $C_2H_5$ | |
| (363) | 4-$OCH_3$ | H | H | O | $OCH_3$ | $OCH_3$ | $CH_3$ | $C_3H_7(n)$ | |
| (364) | " | " | " | " | " | " | $C_2H_5$ | $C_2H_5$ | |
| (365) | " | " | " | " | " | " | $C_3H_7(n)$ | $C_3H_7(n)$ | |
| (366) | " | " | " | " | " | " | $C_4H_9(n)$ | $C_4H_9(n)$ | |
| (367) | 2-$C_2H_5$ | " | " | " | " | " | $CH_3$ | $CH_3$ | |
| (368) | " | " | " | " | " | " | " | $C_2H_5$ | |
| (369) | " | " | " | " | " | " | " | $C_3H_7(n)$ | |
| (370) | " | " | " | " | " | " | $C_2H_5$ | $C_2H_5$ | |
| (371) | " | " | " | " | " | " | $C_3H_7(n)$ | $C_3H_7(n)$ | |
| (372) | " | " | " | " | " | " | $C_4H_9(n)$ | $C_4H_9(n)$ | |
| (373) | 3-$C_3H_7(n)$ | " | " | " | " | " | $CH_3$ | $CH_3$ | |
| (374) | " | " | " | " | " | " | " | $C_2H_5$ | |
| (375) | 3-$C_3H_7(n)$ | H | H | O | $OCH_3$ | $OCH_3$ | $CH_3$ | $C_3H_7(n)$ | |
| (376) | " | " | " | " | " | " | $C_2H_5$ | $C_2H_5$ | |
| (377) | " | " | " | " | " | " | $C_3H_7(n)$ | $C_3H_7(n)$ | |
| (378) | " | " | " | " | " | " | $C_4H_9(n)$ | $C_4H_9(n)$ | |
| (379) | 4-$C_4H_9(n)$ | " | " | " | " | " | $CH_3$ | $CH_3$ | |
| (380) | " | " | " | " | " | " | " | $C_2H_5$ | |
| (381) | " | " | " | " | " | " | " | $C_3H_7(n)$ | |
| (382) | " | " | " | " | " | " | $C_2H_5$ | $C_2H_5$ | |
| (383) | " | " | " | " | " | " | $C_3H_7(n)$ | $C_3H_7(n)$ | |
| (384) | " | " | " | " | " | " | $C_4H_9(n)$ | $C_4H_9(n)$ | |
| (385) | 2-$OC_2H_5$ | " | " | " | " | " | $CH_3$ | $CH_3$ | |
| (386) | " | " | " | " | " | " | " | $C_2H_5$ | |
| (387) | 2-$OC_2H_5$ | H | H | O | $OCH_3$ | $OCH_3$ | $CH_3$ | $C_3H_7(n)$ | |
| (388) | " | " | " | " | " | " | $C_2H_5$ | $C_2H_5$ | |
| (389) | " | " | " | " | " | " | $C_3H_7(n)$ | $C_3H_7(n)$ | |
| (390) | " | " | " | " | " | " | $C_4H_9(n)$ | $C_4H_9(n)$ | |
| (391) | 3-$OC_3H_7(i)$ | " | " | " | " | " | $CH_3$ | $CH_3$ | |
| (392) | " | " | " | " | " | " | " | $C_2H_5$ | |
| (393) | " | " | " | " | " | " | " | $C_3H_7(n)$ | |
| (394) | " | " | " | " | " | " | $C_2H_5$ | $C_2H_5$ | |
| (395) | " | " | " | " | " | " | $C_3H_7(n)$ | $C_3H_7(n)$ | |
| (396) | " | " | " | " | " | " | $C_4H_9(n)$ | $C_4H_9(n)$ | |
| (397) | 4-$OC_4H_9(n)$ | " | " | " | " | " | $CH_3$ | $CH_3$ | |
| (398) | " | " | " | " | " | " | " | $C_2H_5$ | |
| (399) | 4-$OC_4H_9(n)$ | H | H | O | $OCH_3$ | $OCH_3$ | $CH_3$ | $C_3H_7(n)$ | |
| (400) | " | " | " | " | " | " | $C_2H_5$ | $C_2H_5$ | |
| (401) | " | " | " | " | " | " | $C_3H_7(n)$ | $C_3H_7(n)$ | |
| (402) | " | " | " | " | " | " | $C_4H_9(n)$ | $C_4H_9(n)$ | |

TABLE 2-continued

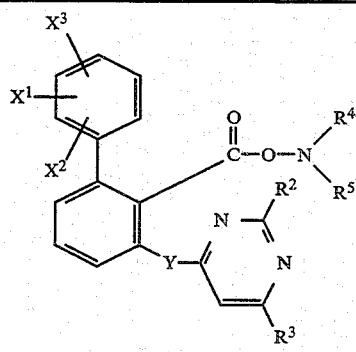

| Compound No. | X¹ | X² | X³ | Y | R² | R³ | R⁴ | R⁵ | Physical properties |
|---|---|---|---|---|---|---|---|---|---|
| (403) | 2-F | 4-F | " | " | " | " | CH₃ | CH₃ | |
| (404) | " | " | " | " | " | " | " | C₂H₅ | |
| (405) | " | " | " | " | " | " | C₂H₅ | " | |
| (406) | " | " | " | " | " | " | C₃H₇(n) | C₃H₇(n) | |
| (407) | 2-Cl | 4-Cl | " | " | " | " | CH₃ | CH₃ | |
| (408) | " | " | " | " | " | " | " | C₂H₅ | |
| (409) | " | " | " | " | " | " | C₂H₅ | " | |
| (410) | " | " | " | " | " | " | C₃H₇(n) | C₃H₇(n) | |
| (411) | 2-F | 6-F | " | " | " | " | CH₃ | CH₃ | |
| (412) | 2-F | 6-F | H | O | OCH₃ | OCH₃ | CH₃ | C₂H₅ | |
| (413) | " | " | " | " | " | " | C₂H₅ | " | |
| (414) | " | " | " | " | " | " | C₃H₇(n) | C₃H₇(n) | |
| (415) | 2-Cl | 6-Cl | " | " | " | " | CH₃ | CH₃ | |
| (416) | " | " | " | " | " | " | " | C₂H₅ | |
| (417) | " | " | " | " | " | " | C₂H₅ | C₂H₅ | |
| (418) | " | " | " | " | " | " | C₃H₇(n) | C₃H₇(n) | |
| (419) | " | 4-F | " | " | " | " | CH₃ | CH₃ | |
| (420) | " | " | " | " | " | " | " | C₂H₅ | |
| (421) | " | " | " | " | " | " | C₂H₅ | " | |
| (422) | " | " | " | " | " | " | C₃H₇(n) | C₃H₇(n) | |
| (423) | " | 6-F | " | " | " | " | CH₃ | CH₃ | |
| (424) | 2-Cl | 6-F | H | O | OCH₃ | OCH₃ | CH₃ | C₂H₅ | |
| (425) | " | " | " | " | " | " | C₂H₅ | " | |
| (426) | " | " | " | " | " | " | C₃H₇(n) | C₃H₇(n) | |
| (427) | 3-Cl | 5-Cl | " | " | " | " | CH₃ | CH₃ | |
| (428) | " | " | " | " | " | " | " | C₂H₅ | |
| (429) | " | " | " | " | " | " | C₂H₅ | " | |
| (430) | " | " | " | " | " | " | C₃H₇(n) | C₃H₇(n) | |
| (431) | 4-Cl | 2-OCH₃ | " | " | " | " | CH₃ | CH₃ | |
| (432) | " | " | " | " | " | " | " | C₂H₅ | |
| (433) | " | " | " | " | " | " | C₂H₅ | " | |
| (434) | " | " | " | " | " | " | C₃H₇(n) | C₃H₇(n) | |
| (435) | 2-Cl | 4-Cl | 6-Cl | " | " | " | CH₃ | CH₃ | |
| (436) | 2-Cl | 4-Cl | 6-Cl | O | OCH₃ | OCH₃ | CH₃ | C₂H₅ | |
| (437) | " | " | " | " | " | " | C₂H₅ | " | |
| (438) | " | " | " | " | " | " | C₃H₇ | C₃H₇(n) | |
| (439) | " | 3-Cl | 5-Cl | " | " | " | CH₃ | CH₃ | |
| (440) | " | " | " | " | " | " | " | C₂H₅ | |
| (441) | " | " | " | " | " | " | C₂H₅ | " | |
| (442) | " | " | " | " | " | " | C₃H₇ | C₃H₇(n) | |
| (443) | 2-CH₃ | 4-CH₃ | 6-CH₃ | " | " | " | CH₃ | CH₃ | |
| (444) | " | " | " | " | " | " | " | C₂H₅ | |
| (445) | " | " | " | " | " | " | C₂H₅ | " | |
| (446) | " | " | " | " | " | " | C₃H₇ | C₃H₇(n) | |
| (447) | " | 3-CH₃ | 4-OCH₃ | " | " | " | CH₃ | CH₃ | |
| (448) | 2-CH₃ | 3-CH₃ | 4-OCH₃ | O | OCH₃ | OCH₃ | CH₃ | C₂H₅ | |
| (449) | " | " | " | " | " | " | C₂H₅ | " | |
| (450) | " | " | " | " | " | " | C₃H₇ | C₃H₇(n) | |
| (451) | H | H | H | O | Cl | SCH₃ | CH₃ | CH₃ | |
| (452) | " | " | " | " | OCH₃ | " | " | " | |
| (453) | " | " | " | " | CH₃ | " | " | " | |
| (454) | 2-NO₂ | " | " | " | OCH₃ | OCH₃ | " | " | |
| (455) | 3-NO₂ | " | " | " | " | " | " | " | |
| (456) | 4-NO₂ | " | " | " | " | " | " | " | |
| (457) | 2-CN | " | " | " | " | " | " | " | |
| (458) | 3-CN | " | " | " | " | " | " | " | |
| (459) | 4-CN | " | " | " | " | " | " | " | |
| (460) | 2-NO₂ | 4-CH₃ | 6-CN | O | OCH₃ | OCH₃ | CH₃ | CH₃ | |
| (461) | H | H | H | " | " | OCHF₂ | " | " | |
| (462) | " | " | " | S | OCF₃ | OCF₃ | ⁺(CH₂)₅ | | |
| (463) | " | " | " | O | SCH₃ | Cl | ⁺(CH₂)₅ | | $n_D^{24}$ 1.5896 |
| (464) | 2-OH | " | " | H | OCH₃ | OCH₃ | CH₃ | CH₃ | |
| (465) | 3-OH | " | " | " | " | " | " | " | |

TABLE 2-continued

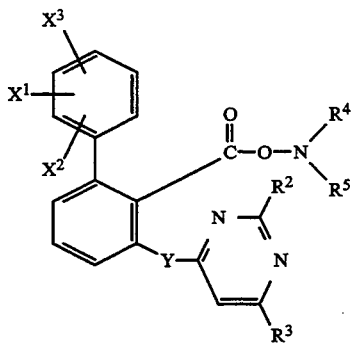

| Compound No. | $X^1$ | $X^2$ | $X^3$ | Y | $R^2$ | $R^3$ | $R^4$ | $R^5$ | Physical properties |
|---|---|---|---|---|---|---|---|---|---|
| (466) | 4-OH | " | " | " | " | " | " | " | |
| (467) | 2-CH$_3$ | 4-CH$_3$ | 6-CH$_3$ | O | OCH$_3$ | OCH$_3$ | CH$_2$—C$_6$H$_5$ | CH$_2$—C$_6$H$_5$ | $n_D^{24}$ 1.5521 |
| (468) | " | " | " | " | " | " | ⟨CH$_2$⟩$_5$ | | $n_D^{24}$ 1.5253 |
| (469) | 3-Cl | H | H | " | " | " | CH$_2$—C$_6$H$_5$ | CH$_2$—C$_6$H$_5$ | $n_D^{24}$ 1.5865 |
| (470) | " | " | " | " | " | " | ⟨CH$_2$⟩$_5$ | | $n_D^{24}$ 1.5557 |
| (471) | H | H | H | O | SCH$_3$ | Cl | C$_2$H$_5$ | C$_2$H$_5$ | m.p. 123.7° C. (decomposition) |
| (472) | 2-CF$_3$ | " | " | " | OCH$_3$ | OCH$_3$ | CH$_3$ | CH$_3$ | |
| (473) | 3-CF$_3$ | " | " | " | " | " | " | " | |
| (474) | 4-CF$_3$ | " | " | " | " | " | " | " | |
| (475) | " | " | " | " | " | " | C$_2$H$_5$ | C$_2$H$_5$ | |

The production of biphenyl derivative of (IV) which is the starting material is shown as a reference example.

REFERENCE EXAMPLE 1

2.41 Grams of 60% sodium hydride in oil was suspended in 100 ml of N,N-dimethylformamide and to the suspension was added gradually 17.44 g of benzyl 6-phenylsalicylate dissolved in 50 ml of N,N-dimethylformamide. Then, the mixture was stirred at room temperature for 30 minutes. To the reaction system was added 10.01 g of 4-chloro-2,6-dimethoxypyrimidine in 50 ml of N,N-dimethylformamide and the reaction mixture was heated at 100°–110° C. with stirring for 3 hours. After cooling on standing, the reaction mixture was poured into 1N hydrochloric acid and extracted with ethyl acetate. The organic layer separated from the aqueous layer was washed with aqua. saturated sodium chloride solution three times and the organic layer was dried over anhydrous magnesium sulfate. The solvent was removed under reduced pressure and the residue obtained was subjected to silica gel column chromatography (hexane/ethyl acetate (10:1–3:1, v/v) to obtain 21.55 g of benzyl 2-(2,6-dimethoxypyrimidine-4-yloxy)-6-phenylbenzoate.

$^1$H-NMR (CDCl$_3$): δ3.77 (s, 3H) 3.87 (s, 3H) 4.89 (S, 2H) 5.65 (S, 1H) 6.76~7.43 (m, 13H)

Formulation examples are shown below. In the examples, the present compound (I) is shown by Compound No. in Tables 1 and 2 and parts are by weight.

FORMULATION EXAMPLE 1

Fifty parts of any one of the present compounds (1)–(479), 3 parts of calcium lignosulfonate, 2 parts of sodium lauryl sulfate and 45 parts of synthetic hydrated silicon dioxide are well mixed while being powdered to obtain a wettable powder.

FORMULATION EXAMPLE 2

Ten parts of any one of the present compounds (1)–(479), 14 parts of polyoxyethylene styrylphenyl ether, 6 parts of calcium dodecylbenzenesulfonate, 35 parts of xylene and 35 parts of cyclohexanone are well mixed to obtain an emulsifiable concentrate.

FORMULATION EXAMPLE 3

Two parts of any one of the present compounds (1)–(479), 2 parts of synthetic hydrated silicon dioxide, 2 parts of calcium lignosulfonate, 30 parts of bentonite and 64 parts of kaolin clay are well pulverized and mixed. The resulting mixture is well kneaded with water, granulated and dried to obtain a granule.

FORMULATION EXAMPLE 4

Twenty five parts of any one of the present compounds (1)–(479), 50 parts of polyvinyl alcohol (10% aq.) and 25 parts of water are mixed and wet-pulverized until the particle size decreases to 5 microns or less. Thus, a suspension formulation is obtained.

FORMULATION EXAMPLE 5

1 Part of any one of the present compounds (2)–(11), (13)–(15), (25)–(28), (30)–(33), (35)–(38), (40)–(43), (45)–(48), (50)–(53), (55)–(58), (60)–(63), (65)–(68), (70)–(73), (75)–(78), (80)–(83), (85), (87)–(89), (91)–(94), (96)–(99), (101)–(104), (106)–(109), (111)–(114), (116)–(119), (121)–(124), (126)–(129), (131)–(134), (136)–(139), (141)–(144), (146)–(149), (151)–(154), (156)–(159), (161)–(164), (166)–(169), (171)–(174), (178)–(179), (182)–(184), (185), (192), (193), (195)–(198), (200)–(203), (205)–(208), 1 part of polyoxyethylene styrylphenyl ether and 98 parts of water are well mixed to obtain a liquid formulation.

It is shown by test examples that the present compounds are useful as an active ingredient for herbicides. In the examples, the present compound (I) is shown by compound No. in Tables 1 and 2, and compounds used for comparison are shown by Compound symbol in Table 3.

TABLE 3

| Compound symbol | Structural formula | Remarks |
|---|---|---|
| A | (structure: chlorophenyl with COOH, OMe, N=, O, N, OMe groups) | EP 346789 (1.020) |
| B | (structure: biphenyl with COOH, OMe, N, O, N, OMe groups) | EP 402751 (1.004) |

The herbicidal activity and phytotoxicity were evaluated in six stages, 0, 1, 2, 3, 4 and 5 by comparing germination and growth of test plants with those untreated.

[0]: the states of germination and growth of test plants showed no difference.

[5]: test plants either completely died or germination/growth were totally inhibited.

Test Example 1 Soil surface treatment test in upland field

Cylindrical plastic pots of 10 cm in diameter and 10 cm in depth were filled with upland field soil, and seeds of plants in Table 4 were sowed in the pots and covered with soil. The test compounds (2), (3), (9) were formulated into liquid formulations and the others were formulated into emulsifiable concentrates according to Formulation Example 2 or 5, and the prescribed amount of each emulsifiable concentrate and liquid formulation was diluted with water at spray volume of 1000 liters/hectare and uniformly applied onto the whole soil surface by means of a sprayer. After application, the test plants were cultivated for 19 days in a greenhouse, and the herbicidal activity was examined. The results are shown in Table 4.

TABLE 4

| Test compound | Dosage rate of active ingredient (g/ha) | Herbicidal activity | |
|---|---|---|---|
| | | Barnyardglass | Ivyleaf morningglory |
| (1) | 500 | 5 | 4 |
| (2) | 500 | 5 | 4 |
| (3) | 500 | 5 | 4 |
| (9) | 500 | 5 | 5 |
| (84) | 500 | 5 | 4 |
| (217) | 500 | 5 | 4 |
| (236) | 500 | 4 | 4 |
| (242) | 500 | 5 | 4 |
| (266) | 500 | 5 | 4 |
| A | 500 | 2 | 0 |

Test Example 2 Foliar treatment test in upland field

Cylindrical plastic pots of 10 cm in diameter and 10 cm in depth were filled with upland field soil, and the seeds of plants in Table 5 were sowed in the respective pots and cultivated for 7 days in a greenhouse.

Thereafter, the test compounds (2), (3), (9) were formulated into liquid formulations and the others were formulated into emulsifiable concentrates according to Formulation Example 2 or 5 and the prescribed amount of each emulsifiable concentrate and liquid formulation was diluted with a spreading agent-containing water at spray volume of 1000 liters/hectare and uniformly applied from above onto the whole foliar portion of the test plant by means of a sprayer. After application, the test plants were cultivated for 19 days in a greenhouse, and the herbicidal activity was examined. The results are shown in Table 5.

TABLE 5

| Test compound | Dosage rate of active ingredient (g/ha) | Herbicidal activity | |
|---|---|---|---|
| | | Ivyleaf morningglory | Wild radish |
| (1) | 125 | 5 | 5 |
| (2) | 125 | 4 | 5 |
| (3) | 125 | 4 | 5 |
| (9) | 125 | 4 | 5 |
| (84) | 125 | 4 | 4 |
| (217) | 125 | 4 | 5 |
| (236) | 125 | 4 | 5 |
| (242) | 125 | 4 | 5 |
| (266) | 125 | 4 | 5 |
| A | 125 | 3 | 2 |

Test Example 3 Flooding treatment test in paddy field

Cylindrical plastic pots of 8 cm in diameter and 12 cm in depth were filled with paddy field soil, and seeds of *Scirpus juncoides* were sowed 1 to 2 cm deep under the soil surface. After creating the state of paddy field by flooding, a tuber of *Sagittaria pygmaea* was buried 1 to 2 cm deep under the soil surface and a rice plant (at the 2-leaf stage) was transplanted and cultivated in a greenhouse. After 6 days (at the initial stage of generation of every weed), the test compound (9) was formulated into liquid formulation and the others were formulated into emulsifiable concentrates according to Formulation Example 2 or 5, and the prescribed amount of each emulsifiable concentrate and liquid formulation was diluted with 5 ml of water and applied onto the water surface. After application, the test plants were cultivated for 19 days in a greenhouse, and the herbicidal activity was examined. The results are shown in Table 6.

TABLE 6

| Test compound | Dosage rate of active ingredient (g/ha) | Phyto-toxicity Rice | Herbicidal activity | |
|---|---|---|---|---|
| | | | Scirpus juncoides | Sagittaria pygmaea |
| (1) | 4 | 0 | 4 | 4 |
| (9) | 4 | 1 | 4 | 4 |
| (217) | 4 | 0 | 4 | 4 |
| A | 4 | 0 | 0 | 3 |

Test Example 4 Soil treatment test in upland field

Vats of 33×23 cm² in area and 11 cm in depth were filled with upland field soil, and the seeds of the test plant shown in Table 7 were sowed in the respective vats and covered with soil in a thickness of 1 to 2 cm. The test compounds were formulated into emulsifiable concentrates according to Formulation Example 2, and the prescribed amount of each emulsifiable concentrate was diluted with water at spray volume of 1000 liters/hectare and uniformly applied onto the whole soil surface by means of a sprayer. After application, the test plants were cultivated for 25 days in a greenhouse, and the herbicidal activity and phytotoxicity were examined. The results are shown in Table 7.

TABLE 7

| Test compound | Dosage rate of active ingredient (g/ha) | Phytotoxicity Wheat | Phytotoxicity Barley | Herbicidal activity Pale smartweed | Herbicidal activity Catchweed bedstraw | Herbicidal activity Blackgrass |
|---|---|---|---|---|---|---|
| (1) | 4 | 0 | 0 | 4 | 4 | 4 |
| (217) | 4 | 0 | 0 | 4 | 4 | 4 |
| (236) | 4 | 0 | 0 | 5 | 4 | 4 |
| (266) | 4 | 0 | 0 | 5 | 4 | 4 |
| B | 4 | 1 | 0 | 2 | 0 | 2 |

Test Example 5 Foliar treatment test in upland field

Vats of 33×23 cm² in area and 11 cm in depth were filled with upland field soil, and seeds of test plants shown in Table 8 were sowed in the respective vats and cultivated for 30 days. Thereafter, the test compounds (2), (3), (9) were formulated into liquid formulations and the others were formulated into emulsifiable concentrates according to Formulation Example 2 or 5, and the prescribed amount of each emulsifiable concentrate and liquid formulation was diluted with water at spray volume of 1000 liters/hectare and uniformly applied from above onto the whole foliar portion of the test plants by means of a sprayer. The conditions of growth of the weed and crops at that time varied depending upon the kind of the test plants, but the test plants were in the 1- to 4-leaf stage and were 2 to 12 cm in height. 25 days after application, the herbicidal activity and phytotoxicity were examined. The results are shown in Table 8. This test was carried out in a greenhouse through the whole test period.

TABLE 8

| Test compound | Dosage rate of active ingredient (g/ha) | Phytotoxicity Wheat | Phytotoxicity Barley | Herbicidal activity Common chickweed | Herbicidal activity Catchweed bedstraw | Herbicidal activity Blackgrass |
|---|---|---|---|---|---|---|
| (1) | 4 | 1 | 1 | 4 | 4 | 4 |
| (2) | 4 | 1 | 2 | 4 | 4 | 4 |
| (3) | 4 | 1 | 1 | 4 | 4 | 4 |
| (9) | 4 | 1 | 1 | 4 | 4 | 4 |
| (236) | 8 | 1 | 1 | 4 | 4 | 4 |
| (242) | 8 | 0 | 1 | 4 | 4 | 4 |
| (266) | 8 | 1 | 2 | 4 | 4 | 4 |
| B | 8 | 4 | 3 | 3 | 3 | 3 |

What is claimed is:
1. A biphenyl derivative represented by the formula (I),

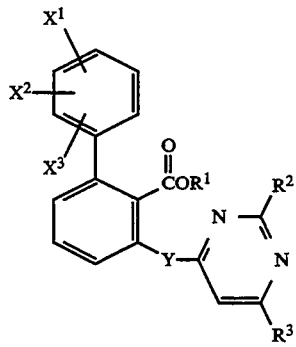

wherein $R^1$ represents a hydrogen atom or a group represented by the formula

(wherein each of $R^4$ and $R^5$ which may be the same or different, represents a hydrogen atom, a $C_1$-$C_6$ alkyl group, a $C_3$-$C_8$ cycloalkyl group, or a phenyl group optionally substituted with at least one member selected from the group consisting of $C_1$-$C_6$ alkyl groups, halogen atoms and $C_1$-$C_6$ alkoxy groups, or a benzyl group optionally substituted with at least one member selected from the group consisting of $C_1$-$C_6$ alkyl groups, halogen atoms and $C_1$-$C_6$ alkoxy groups, or $R^4$ and $R^5$ are bonded together at their ends to form a $C_4$-$C_6$ alkylene group optionally substituted with $C_1$-$C_6$ alkyl groups; or $R^4$ and $R^5$ are bonded together at their ends to form

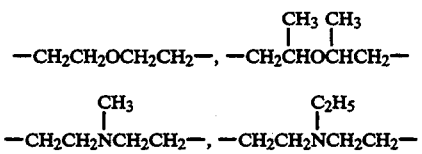

-continued

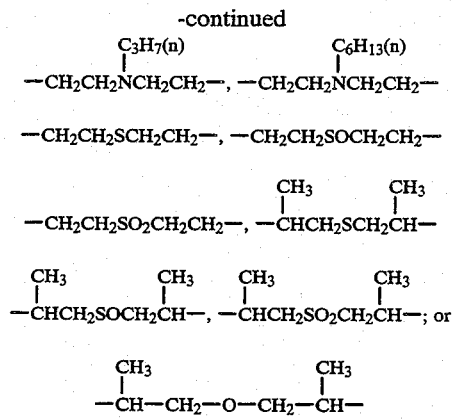

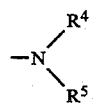

each of $R^2$ and $R^3$, which may be the same or different, represents a $C_1$–$C_6$ alkyl group, a $C_1$–$C_6$ alkoxy group, a $C_1$–$C_6$ alkylthio group, a halo $C_1$–$C_6$ alkoxy group or a halogen atom, each of $X^1$, $X^2$ and $X^3$, which may be the same or different, represents a hydrogen atom, a hydroxyl group, a $C_1$–$C_6$ alkyl group, a halo $C_1$–$C_6$ alkyl group, a $C_1$–$C_6$ alkoxy group, a nitro group, a cyano group or a halogen atom and Y represents an oxygen atom or a sulfur atom; or agriculturally acceptable salts thereof.

2. A biphenyl derivative according to claim 1, wherein $R^1$ represents a group $$-N\begin{matrix}R^4\\R^5\end{matrix}$$

(wherein $R^4$ and $R^5$ are as defined in claim 1).

3. A biphenyl derivative according to claim 1, wherein $R^1$ represents a hydrogen atom or agriculturally acceptable salts thereof.

4. A biphenyl derivative according to claim 1, wherein each of $R^2$ and $R^3$, which may be the same or different, represents a $C_1$–$C_6$ alkoxy group.

5. A biphenyl derivative according to claim 4, wherein each of $R^2$ and $R^3$ represents a methoxy group.

6. A biphenyl derivative according to claim 1, wherein Y represents an oxygen atom.

7. A biphenyl derivative according to claim 2, wherein each of $R^4$ and $R^5$, which may be the same or different, is a $C_1$–$C_3$ alkyl group.

8. A biphenyl derivative according to claim 1, wherein each of $R^2$ and $R^3$, which may be the same or different, represents a $C_1$–$C_6$ alkyl group, a $C_1$–$C_6$ alkoxy group, a halo $C_1$–$C_6$ alkoxy group or a halogen atom, each of $X^1$, $X^2$ and $X^3$, which may be the same or different, represents a hydrogen atom, a $C_1$–$C_6$ alkyl group, a $C_1$–$C_6$ alkoxy group, a halogen atom or a halo $C_1$–$C_6$ alkyl group; or agriculturally acceptable salts thereof.

9. A biphenyl derivative according to claim 2, wherein each of $R^2$ and $R^3$, which may be the same or different, represents a $C_1$–$C_6$ alkyl group, a $C_1$–$C_6$ alkoxy group, a halo $C_1$–$C_6$ alkoxy group or halogen atom, and each of $X^1$, $X^2$ and $X^3$, which may be the same or different, represents a hydrogen atom, a $C_1$–$C_6$ alkyl group, a $C_1$–$C_6$ alkoxy group or halogen atom.

10. A biphenyl derivative according to claim 3, wherein each of $R^2$ and $R^3$, which may be the same or different, represents a $C_1$–$C_6$ alkyl group, a $C_1$–$C_6$ alkoxy group, a halo $C_1$–$C_6$ alkoxy group or halogen atom, and each of $X^1$, $X^2$ and $X^3$, which may be the same or different, represents a hydrogen atom, a $C_1$–$C_6$ alkyl group, a $C_1$–$C_6$ alkoxy group or halogen atom.

11. A herbicidal composition which comprises as an active ingredient, a herbicidally effective amount of the biphenyl derivative (I) according to claim 1 and an inert carrier or a diluent.

12. A method for controlling undesired weeds, which comprises applying a herbicidally effective amount of the biphenyl derivative (I) according to claim 1 to the area where undesired weeds grow or will grow.

* * * * *